(12) United States Patent
Ushikura et al.

(10) Patent No.: US 11,735,622 B2
(45) Date of Patent: Aug. 22, 2023

(54) RADIOGRAPHIC IMAGING APPARATUS

(71) Applicant: FUJIFILM CORPORATION, Tokyo (JP)

(72) Inventors: Shinichi Ushikura, Kanagawa (JP); Naoto Iwakiri, Kanagawa (JP); Keiichi Akamatsu, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 185 days.

(21) Appl. No.: 17/485,525

(22) Filed: Sep. 27, 2021

(65) Prior Publication Data

US 2022/0013572 A1 Jan. 13, 2022

Related U.S. Application Data

(63) Continuation of application No. PCT/JP2020/014680, filed on Mar. 30, 2020.

(30) Foreign Application Priority Data

Mar. 29, 2019 (JP) .................................. 2019-069077
Dec. 27, 2019 (JP) .................................. 2019-239567

(51) Int. Cl.
*H01L 27/146* (2006.01)
*G01T 1/20* (2006.01)
*A61B 6/00* (2006.01)

(52) U.S. Cl.
CPC .......... *H01L 27/14663* (2013.01); *A61B 6/00* (2013.01); *G01T 1/20* (2013.01);
(Continued)

(58) Field of Classification Search
CPC .......... A61B 6/00; G01T 1/20; G01T 1/20183; G01T 1/20184; G01T 1/20188;
(Continued)

(56) References Cited

U.S. PATENT DOCUMENTS 6,259,098 B1 7/2001 Vafi et al.
2014/0001366 A1* 1/2014 Nishida ................ C09K 11/628
250/366
(Continued)

FOREIGN PATENT DOCUMENTS

JP 2001-27672 A 1/2001
JP 2010-78542 A 4/2010
(Continued)

OTHER PUBLICATIONS

International Search Report issued in International Application No. PCT/JP2020/014680 dated Jun. 9, 2020.
(Continued)

*Primary Examiner* — Mark R Gaworecki
(74) *Attorney, Agent, or Firm* — Solaris Intellectual Property Group, PLLC

(57) ABSTRACT

A radiographic imaging apparatus including: a sensor substrate in which pixels are formed in a first surface of a base material; a conversion layer provided on the first surface; a signal processing substrate provided on one side the sensor substrate and includes at least a part of a signal processing unit; a driving substrate provided on the one side or the other side of the sensor substrate and includes at least a part of a drive unit; a first cable of which one end is connected to the sensor substrate and the other end is electrically connected to the signal processing substrate; and a second cable of which one end is connected to the sensor substrate, and passes through the first surface side or a second surface side of the base material and the other end is connected to the driving substrate.

25 Claims, 26 Drawing Sheets

(52) U.S. Cl.
CPC ...... *G01T 1/20183* (2020.05); *G01T 1/20184* (2020.05); *G01T 1/20188* (2020.05); *H01L 27/14636* (2013.01); *H01L 27/14658* (2013.01)

(58) Field of Classification Search
CPC ......... H01L 27/14636; H01L 27/14658; H01L 27/14663
See application file for complete search history.

(56) References Cited

U.S. PATENT DOCUMENTS

| | | |
|---|---|---|
| 2015/0253436 A1 | 9/2015 | Eguchi |
| 2016/0178767 A1 | 6/2016 | Eguchi |
| 2017/0307769 A1 | 10/2017 | Eguchi |
| 2018/0275290 A1 | 9/2018 | Ushikura et al. |
| 2018/0275292 A1* | 9/2018 | Akamatsu ............... G06T 11/00 |

FOREIGN PATENT DOCUMENTS

| | | | |
|---|---|---|---|
| JP | 2015-169625 A | 9/2015 |
| JP | 2018-159611 A | 10/2018 |
| JP | 2019-007748 A | 1/2019 |
| WO | 2010/070735 A1 | 6/2010 |

OTHER PUBLICATIONS

Written Opinion of the ISA issued in International Application No. PCT/JP2020/014680 dated Jun. 9, 2020.

\* cited by examiner

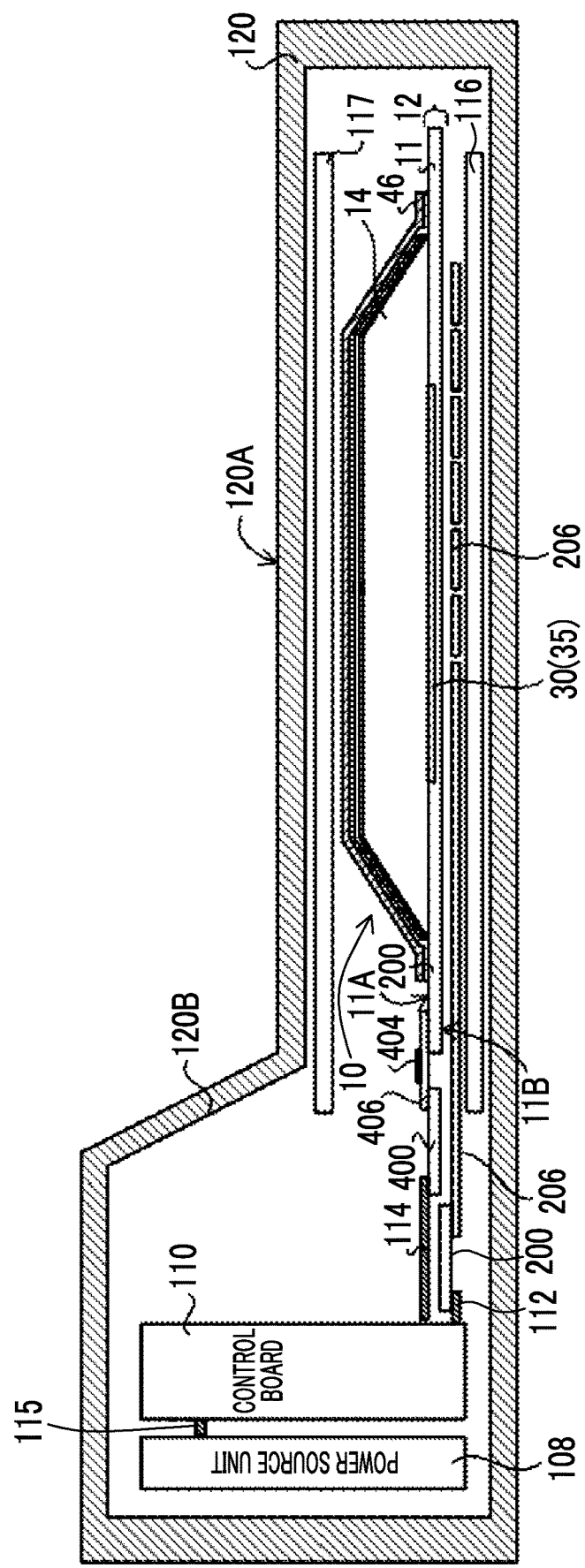

RADIOGRAPHIC IMAGING APPARATUS

CROSS-REFERENCE TO RELATED APPLICATIONS

This application is a continuation application of International Application No. PCT/JP2020/014680, filed on Mar. 30, 2020, the disclosure which is incorporated herein by reference in its entirety. Further, this application claims priority from Japanese Patent Application No. 2019-069077, filed on Mar. 29, 2019, and Japanese Patent Application No. 2019-239567, filed on Dec. 27, 2019, the disclosures of which are incorporated by reference herein in their entireties.

BACKGROUND

Technical Field

The present disclosure relates to a radiographic imaging apparatus.

Description of the Related Art

In the related art, radiographic imaging apparatuses that perform radiographic imaging for medical diagnosis have been known. A radiation detector for detecting radiation transmitted through a subject and generating a radiographic image is used for such radiographic imaging apparatuses.

As this type of radiation detector, there is one comprising a conversion layer, such as a scintillator, which converts radiation into light, and a sensor substrate in which a plurality of pixels, which accumulate electric charges generated in response to light converted in the conversion layer, are provided in a pixel region of a base material. There is known that the radiographic imaging apparatuses comprise a signal processing substrate including a circuit of a signal processing unit that generates image data in response to the electric charges accumulated in the plurality of pixels of the radiation detector, and a driving substrate including a circuit of a drive unit that outputs a drive signal for outputting an electric charge accumulated from each of the plurality of pixels of the sensor substrate, to each of the plurality of pixels.

For example, WO2010/070735A describes a radiographic imaging apparatus in which a signal processing IC and a driving IC are mounted on an end portion of a flexible substrate on which a plurality of pixels are formed and the end portion of the flexible substrate on which each of the signal processing IC and the driving IC is mounted have a shape that is folded to a side opposite to a side on which a conversion layer is formed.

Meanwhile, as the base material of the substrate of the radiation detector, one using a flexible base material is known. By using the flexible base material, for example, the weight of the radiographic imaging apparatuses (radiation detector) can be reduced, and a subject may be easily imaged. However, in the technique described in WO2010/070735A, the sensor substrate, the signal processing IC, and the driving IC are each laminated. Therefore, the thickness cannot be sufficiently reduced.

An object of the present disclosure provides a radiographic imaging apparatus capable of making a portion of the apparatus corresponding to a sensor substrate thinner.

SUMMARY

According to a first aspect of the present disclosure, there is provided a radiographic imaging apparatus comprising a sensor substrate in which a plurality of pixels for accumulating electric charges generated in response to light converted from radiation is formed in a pixel region of a first surface of a flexible base material; a conversion layer that is provided on the first surface of the base material to convert the radiation into light; a signal processing substrate that is provided on one side of a pair of sides of the sensor substrate facing each other and comprises at least a part of a circuit of a signal processing unit to which electrical signals according to the electric charges accumulated in the plurality of pixels of the sensor substrate are input and which generates and outputs image data according to the input electrical signals; a driving substrate that is provided on the one side or the other side of the pair of sides of the sensor substrate and comprises at least a part of a circuit of a drive unit that outputs a drive signal for outputting the accumulated electric charge from each of the plurality of pixels of the sensor substrate, to each of the plurality of pixels; a first cable of which one end is provided along the one side of the pair of sides of the sensor substrate and is electrically connected to the sensor substrate and the other end is electrically connected to the signal processing substrate; and a second cable of which one end is provided along a side intersecting the one side of the pair of sides of the sensor substrate, is electrically connected to the sensor substrate, and passes through the first surface side of the base material or a second surface side opposite to the first surface of the base material and the other end is electrically connected to the driving substrate.

A radiographic imaging apparatus according to a second aspect of the present disclosure is the radiographic imaging apparatus according to the first aspect in which the second cable has a straight shape extending in a straight line, is bent in a direction in which the second cable is folded with respect to an extending direction of the second cable, and is further bent in a direction intersecting the extending direction of the second cable.

A radiographic imaging apparatus according to a third aspect of the present disclosure is the radiographic imaging apparatus according to the first aspect in which the second cable includes a portion that includes one end of the second cable connected to the sensor substrate and extends in a first direction intersecting a direction of the side of the sensor substrate to which the second cable is connected, and a portion that includes the other end of the second cable connected to the driving substrate and extends in a second direction that intersects the first direction.

A radiographic imaging apparatus according to a fourth aspect of the present disclosure is the radiographic imaging apparatus according to the first aspect in which the first cable is mounted with a part of a signal processing circuit, which is not included in the signal processing substrate, in the circuit of the signal processing unit, and the second cable is mounted with a part of a drive circuit, which is not included in the driving substrate, in the circuit of the drive unit.

A radiographic imaging apparatus according to a fifth aspect of the present disclosure is the radiographic imaging apparatus according to the fourth aspect in which the part of the signal processing circuit and the part of the drive circuit are disposed at positions where the parts do not overlap each other.

A radiographic imaging apparatus according to a sixth aspect of the present disclosure is the radiographic imaging apparatus according to the first aspect in which the circuit of the signal processing unit and the circuit of the drive unit are disposed at positions where the circuits do not overlap each other.

A radiographic imaging apparatus according to a seventh aspect of the present disclosure is the radiographic imaging apparatus according to the first aspect in which one end of the second cable is electrically connected to the sensor substrate by a connector at the intersecting side of the sensor substrate.

A radiographic imaging apparatus according to an eighth aspect of the present disclosure is the radiographic imaging apparatus according to the first aspect in which the other end of the second cable is electrically connected to the driving substrate by a connector.

A radiographic imaging apparatus according to a ninth aspect of the present disclosure is the radiographic imaging apparatus according to the first aspect in which the number of the second cables electrically connected to the driving substrate is smaller than the number of the second cables electrically connected to the sensor substrate.

A radiographic imaging apparatus according to a tenth aspect of the present disclosure is the radiographic imaging apparatus according to the first aspect further comprising a relay substrate that is electrically connected to the driving substrate, and the other end of the second cable is electrically connected to the relay substrate instead of the driving substrate.

A radiographic imaging apparatus according to an eleventh aspect of the present disclosure is the radiographic imaging apparatus according to the tenth aspect further comprising a plurality of the second cables having a larger number than the number of the relay substrates.

A radiographic imaging apparatus of a twelfth aspect of the present disclosure is the radiographic imaging apparatus of the tenth aspect in which the relay substrate is electrically connected to at least one of the other end of the second cable or the driving substrate by a connector.

A radiographic imaging apparatus according to a thirteenth aspect of the present disclosure is the radiographic imaging apparatus according to the tenth aspect in which the relay substrate includes a first relay portion that is electrically connected to the second cable, and an L-shaped second relay portion having a long side that extends along a side of the sensor substrate to which the second cable is electrically connected, and a short side that extends in a direction intersecting the direction in which the long side extends and is electrically connected to the driving substrate.

A radiographic imaging apparatus according to a fourteenth aspect of the present disclosure is the radiographic imaging apparatus according to the thirteenth aspect in which the short side of the second relay portion is bent in the direction in which the long side extends.

A radiographic imaging apparatus according to a fifteenth aspect of the present disclosure is the radiographic imaging apparatus according to the tenth aspect in which the relay substrate includes a first relay portion that is electrically connected to the second cable, a second relay portion that extends along a side of the sensor substrate to which the second cable is electrically connected, and a third relay portion of which one end is electrically connected to an end portion of the second relay portion and the other end is electrically connected to the driving substrate.

A radiographic imaging apparatus according to a sixteenth aspect of the present disclosure is the radiographic imaging apparatus according to the fifteenth aspect in which a connecting portion by which the end portion of the second relay portion and the one end of the third relay portion are electrically connected is provided in a region that does not overlap the sensor substrate.

A radiographic imaging apparatus according to a seventeenth aspect of the present disclosure is the radiographic imaging apparatus according to the first aspect further comprising a relay substrate that is electrically connected to the sensor substrate, and one end of the second cable is electrically connected to the relay substrate instead of the sensor substrate.

A radiographic imaging apparatus according to an eighteenth aspect of the present disclosure is the radiographic imaging apparatus according to the seventeenth aspect in which the relay substrate is electrically connected to at least one of the one end of the second cable or the sensor substrate by a connector.

A radiographic imaging apparatus of a nineteenth aspect of the present disclosure is the radiographic imaging apparatus of the seventeenth aspect in which the relay substrate includes a first relay substrate of which one end is electrically connected to the sensor substrate and a second relay substrate of which one end is electrically connected to the other end of the first relay substrate.

A radiographic imaging apparatus according to a twentieth aspect of the present disclosure is the radiographic imaging apparatus according to the nineteenth aspect in which the connecting portion by which the first relay substrate and the second relay substrate are electrically connected to each other is provided in a region that does not overlap the sensor substrate.

A radiographic imaging apparatus according to a twenty-first aspect of the present disclosure is the radiographic imaging apparatus according to any one of the tenth aspect in which the relay substrate has flexibility.

A radiographic imaging apparatus according to a twenty-second aspect of the present disclosure is the radiographic imaging apparatus according to the first aspect in which a shielding member that shields at least one of electricity, magnetism, or radiation is provided between the second cable and the first surface side of the base material through which the second cable passes or the second surface side.

A radiographic imaging apparatus according to a twenty-third aspect of the present disclosure is the radiographic imaging apparatus according to the twenty-second aspect in which the shielding member is also provided between the circuit of the signal processing unit and the circuit of the drive unit.

A radiographic imaging apparatus according to a twenty-fourth aspect of the present disclosure is the radiographic imaging apparatus according to the first aspect further comprising a housing that houses the sensor substrate, the conversion layer, the signal processing substrate, the driving substrate, the first cable, and the second cable.

A radiographic imaging apparatus according to a twenty-fifth aspect of the present disclosure is the radiographic imaging apparatus according to the twenty-fourth aspect in which the housing has an irradiation surface to be irradiated with the radiation, and the second cable passes between a surface of the housing opposite to the irradiation surface and a laminate in which the conversion layer is formed on the sensor substrate.

According to the present disclosure, the portion of the apparatus corresponding to the sensor substrate can be made thinner.

BRIEF DESCRIPTION OF THE DRAWINGS

Exemplary embodiments according to the technique of the present disclosure will be described in detail based on the following figures, wherein:

FIG. 31 is a cross-sectional view of another example of the radiographic imaging apparatus of the embodiment housed in the housing.

DETAILED DESCRIPTION

Hereinafter, embodiments of the present invention will be described in detail with reference to the drawings. In addition, the present embodiments do not limit the present invention.

First Embodiment

The radiation detector of the present embodiment has a function of detecting radiation transmitted through a subject to output image information representing a radiographic image of the subject. The radiation detector of the present embodiment comprises a sensor substrate and a conversion layer that converts radiation into light (refer to a sensor substrate 12 and a conversion layer 14 of the radiation detector 10 in FIG. 2).

In addition, in the radiographic imaging apparatus of the present embodiment, a case where the radiation detector is applied to an irradiation side sampling (ISS) type radiation detector in which radiation R is radiated from the sensor substrate side will be described.

Figure 1:
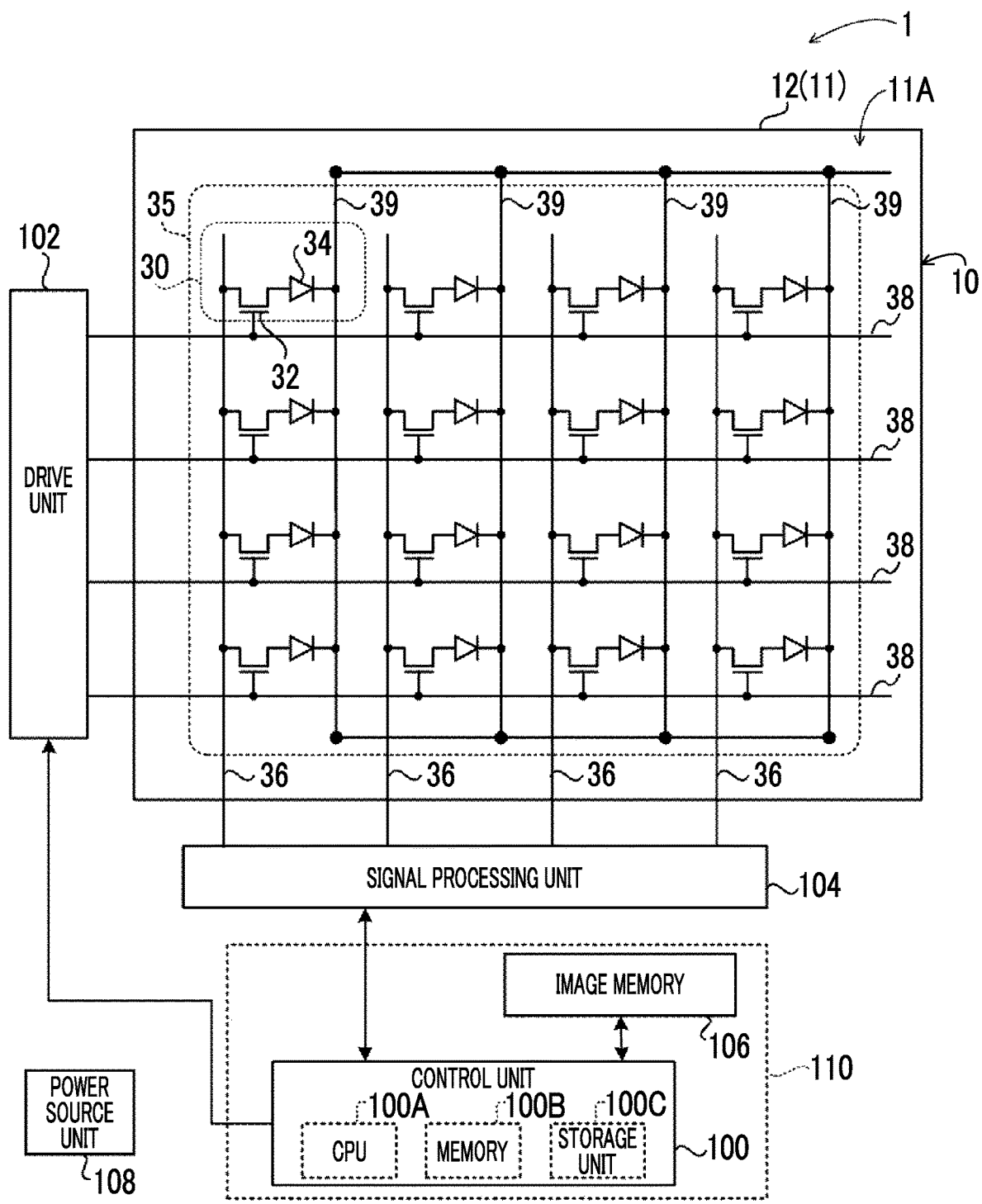
FIG. 1 is a block diagram showing an example of the configuration of main parts of an electrical system in a radiographic imaging apparatus of a first embodiment.

First, the outline of an example of the configuration of an electrical system in a radiographic imaging apparatus of the present embodiment will be described with reference to FIG. 1. FIG. 1 is a block diagram showing an example of the configuration of main parts of the electrical system in the radiographic imaging apparatus of the present embodiment.

As shown in FIG. 1, the radiographic imaging apparatus 1 of the present embodiment comprises the radiation detector 10, a control unit 100, a drive unit 102, a signal processing unit 104, an image memory 106, and a power source unit 108.

The radiation detector 10 comprises a sensor substrate 12 and a conversion layer (refer to FIG. 2) that converts radiation into light. The sensor substrate 12 comprises a flexible base material 11, and a plurality of pixels 30 provided on a first surface 11A of the base material 11. In addition, in the following description, the plurality of pixels 30 may be simply referred to as "pixels 30".

As shown in FIG. 1, each pixel 30 of the present embodiment comprises a sensor unit 34 that generates and accumulates electric charges in response to the light converted by the conversion layer, and a switching element 32 that reads out the electric charges accumulated in the sensor unit 34. In the present embodiment, as an example, a thin film transistor (TFT) is used as the switching element 32. For that reason, in the following description, the switching element 32 is referred to as a "TFT 32". In the present embodiment, a layer in which the pixels 30 are formed on the first surface 11A of the base material 11 is provided as a layer that is formed with the sensor unit 34 and the TFT 32 and is planarized.

The pixels 30 are two-dimensionally arranged in one direction (a scanning wiring direction corresponding to a transverse direction of FIG. 1, hereinafter referred to as a "row direction"), and a direction intersecting the row direction (a signal wiring direction corresponding to the longitudinal direction of FIG. 1, hereinafter referred as a "column direction") in a pixel region 35 of the sensor substrate 12. Although an array of the pixels 30 is shown in a simplified manner in FIG. 1, for example, 1024×1024 pixels 30 are arranged in the row direction and the column direction.

Additionally, a plurality of scanning wiring lines 38, which are provided for respective rows of the pixels 30 to control switching states (ON and OFF) of the TFTs 32, and a plurality of signal wiring lines 36, which are provided for respective columns of the pixels 30 and from which electric charges accumulated in the sensor units 34 are read, are provided in a mutually intersecting manner in the radiation detector 10. Each of the plurality of scanning wiring lines 38 is connected to the drive unit 102 via a flexible cable 206 (refer to FIG. 2), and thereby, a drive signal for driving the TFT 32 output from the drive unit 102 to control the switching state thereof flows through each of the plurality of scanning wiring lines 38. Additionally, each of the plurality of signal wiring lines 36 is connected to the signal processing unit 104 via a flexible cable 406 (refer to FIG. 2), and thereby, electric charges read from the respective pixels 30 are output to the signal processing unit 104 as electrical signals. The signal processing unit 104 generates and outputs image data according to the input electrical signals.

The control unit 100 to be described below is connected to the signal processing unit 104, and the image data output from the signal processing unit 104 is sequentially output to the control unit 100. The image memory 106 is connected to the control unit 100, and the image data sequentially output from the signal processing unit 104 is sequentially stored in the image memory 106 under the control of the control unit 100. The image memory 106 has a storage capacity capable of storing image data equivalent to a predetermined number of sheets, and whenever radiographic images are captured, image data obtained by the capturing is sequentially stored in the image memory 106.

The control unit 100 comprises a central processing unit (CPU) 100A, a memory 100B including a read only memory (ROM), a random access memory (RAM), and the like, and a nonvolatile storage unit 100C, such as a flash memory. An example of the control unit 100 is a microcomputer or the like. The control unit 100 controls the overall operation of the radiographic imaging apparatus 1.

In addition, in the radiographic imaging apparatus 1 of the present embodiment, the image memory 106, the control unit 100, and the like are formed in a control substrate 110.

Additionally, common wiring lines 39 are provided in a wiring direction of the signal wiring lines 36 at the sensor units 34 of the respective pixels 30 in order to apply bias voltages to the respective pixels 30. Bias voltages are applied to the respective pixels 30 from a bias power source by electrically connecting the common wiring lines 39 to the bias power source (not shown) outside the sensor substrate 12 via a terminal (not shown).

The power source unit 108 supplies electrical power to various elements and various circuits, such as the control unit 100, the drive unit 102, the signal processing unit 104, the image memory 106, and the power source unit 108. In addition, in FIG. 1, an illustration of wiring lines, which connect the power source unit 108 and various elements or various circuits together, is omitted in order to avoid complications.

Figure 2:
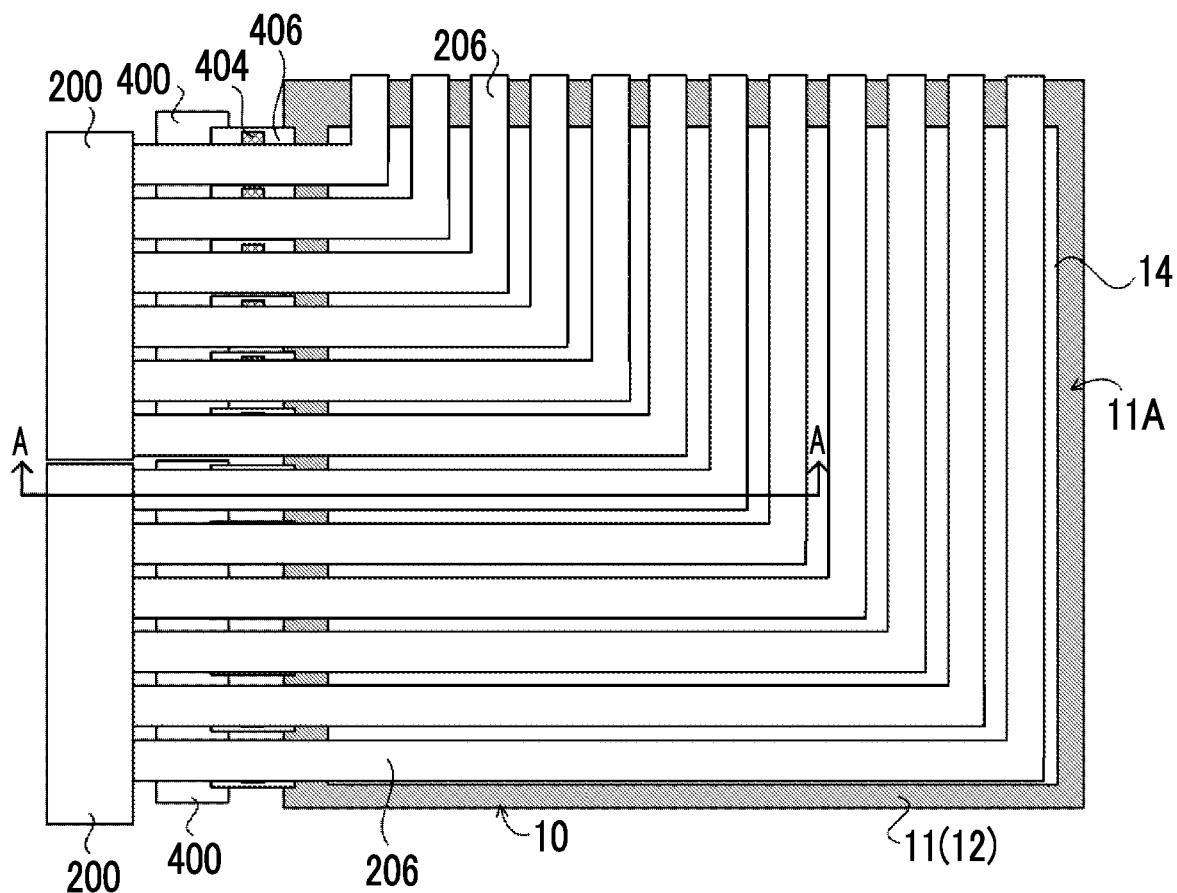
FIG. 2 is a plan view of an example of the radiographic imaging apparatus of the first embodiment as seen from the side on which a conversion layer is provided.
Figure 3:
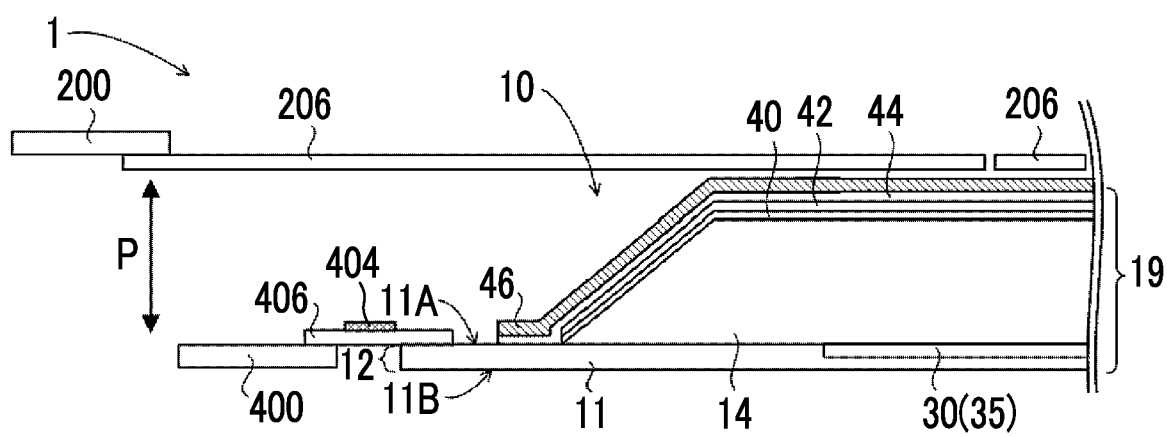
FIG. 3 is a cross-sectional view taken along line A-A of an example of the radiographic imaging apparatus shown in FIG. 2.
Figure 4:
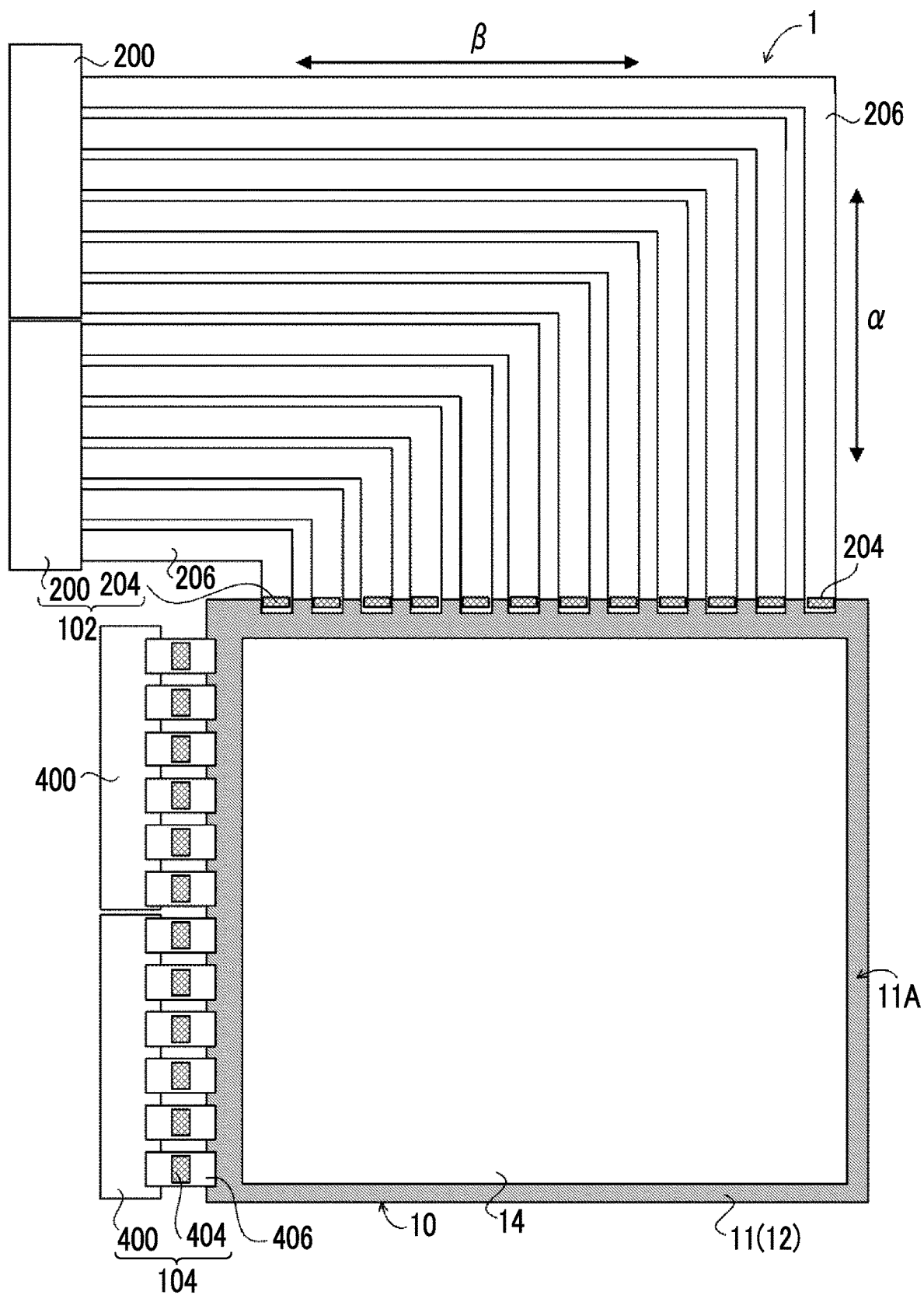
FIG. 4 is a plan view showing an example of a state in which the flexible cable folded in FIG. 2 is unfolded without being folded.

Moreover, the radiographic imaging apparatus 1 will be described in detail. FIG. 2 is a plan view of the radiographic imaging apparatus 1 according to the present embodiment as seen from the first surface 11A side of the base material 11. Additionally, FIG. 3 is a cross-sectional view taken along line A-A of the radiographic imaging apparatus 1 in FIG. 2. Moreover, FIG. 4 shows an example of a state in which the flexible cable 206 folded in FIG. 2 is unfolded without being folded.

The first surface 11A of the base material 11 is provided with a pixel region 35 provided with the above-described pixels 30.

The base material 11 is a resin sheet that has flexibility and includes, for example, a plastic such as a polyimide (PI). The thickness of the base material 11 may be a thickness such that desired flexibility is obtained in response to the hardness of a material, the size of the sensor substrate 12 (the area of the first surface 11A or a second surface 11B), and the like. In a case where a rectangular base material 11 is a single body, an example having flexibility indicates one in which the base material 11 hangs down (is lower than the height of a fixed side) 2 mm or more due to the gravity of the base material 11 resulting from its own weight at a position 10 cm away from the fixed side with one side of the base material 11 fixed. As a specific example in a case where the base material 11 is the resin sheet, the thickness thereof may be 5 μm to 125 μm, and the thickness thereof may be more preferably 20 μm to 50 μm.

In addition, the base material 11 has characteristics capable of withstanding the manufacture of the pixels 30 and has characteristics capable of withstanding the manufacture of amorphous silicon TFT (a-Si TFT) in the present embodiment. As such characteristics of the base material 11, it is preferable that the coefficient of thermal expansion (CTE) at 300° C. to 400° C. is about the same as the coefficient of thermal expansion of amorphous silicon (Si) wafer (for example, ±5 ppm/K). Specifically, the coefficient of thermal expansion of the base material 11 at 300° C. to 400° C. is preferably 20 ppm/K or less. Additionally, as the heat shrinkage percentage of the base material 11, it is preferable that the heat shrinkage percentage at 400° C. is 0.5% or less with the thickness being 25 μm. Additionally, it is preferable that the modulus of elasticity of the base material 11 does not have a transition point that general PI has, in a temperature range of 300° C. to 400° C., and the modulus of elasticity at 500° C. is 1 GPa or more.

Additionally, it is preferable that the base material 11 of the present embodiment has a fine particle layer containing inorganic fine particles having an average particle diameter of 0.05 μm or more and 2.5 μm or less, which absorbs backscattered rays by itself in order to suppress backscattered rays. In addition, as the inorganic fine particles, in the case of the resinous base material 11, it is preferable to use an inorganic material of which the atomic number is larger than the atoms constituting the organic material that is the base material 11 and is 30 or less. Specific examples of such fine particles include $SiO_2$ that is an oxide of Si having an atomic number of 14, MgO that is an oxide of Mg having an atomic number of 12, $Al_2O_3$ that is an oxide of Al having an atomic number of 13, $TiO_2$ that is an oxide of Ti having an atomic number of 22, and the like. A specific example of the resin sheet having such characteristics is XENOMAX (registered trademark).

In addition, the above thicknesses in the present embodiment were measured using a micrometer. The coefficient of thermal expansion was measured according to JIS K7197: 1991. In addition, the measurement was performed by cutting out test pieces from a main surface of the base material 11 while changing the angle by 15 degrees, measuring the coefficient of thermal expansion of each of the cut-out test pieces, and setting the highest value as the coefficient of thermal expansion of the base material 11. The coefficient of thermal expansion is measured at intervals of 10° C. between −50° C. and 450° C. in a machine direction (MD) and a transverse direction (TD), and (ppm/° C.) is converted to (ppm/K). For the measurement of the coefficient of thermal expansion, the TMA4000S apparatus made by MAC Science Co., Ltd. is used, sample length is 10 mm, sample width is 2 mm, initial load is 34.5 $g/mm^2$, temperature rising rate is 5° C./min, and the atmosphere is in argon.

In addition, the base material 11 having desired flexibility is not limited to resinous materials such as the resin sheet. For example, the base material 11 may be a glass substrate or the like having a relatively small thickness. As a specific example of a case where the base material 11 is the glass substrate, generally, in a size of about 43 cm on a side, the glass substrate has flexibility as long as the thickness is 0.3 mm or less. Therefore, any desired glass substrate may be used as long as the thickness is 0.3 mm or less.

As shown in FIGS. 2 to 4, the conversion layer 14 is provided on the pixel region 35 of the present embodiment. The conversion layer 14 is provided on a partial region of the first surface 11A of the base material 11 including the pixel region 35. In this way, the conversion layer 14 of the present embodiment is not provided on the region of an outer peripheral portion on the first surface 11A of the base material 11. In addition, here, the term "on" in the structure of the radiation detector 10 means "on" in a positional relationship with reference to the sensor substrate 12 side. For example, the conversion layer 14 is provided on the sensor substrate 12.

In the present embodiment, a scintillator including CsI (cesium iodide) is used as an example of the conversion layer 14. It is preferable that such a scintillator includes, for example, CsI:T1 (cesium iodide to which thallium is added) or CsI:Na (cesium iodide to which sodium is added) having an emission spectrum of 400 nm to 700 nm at the time of X-ray radiation. In addition, the emission peak wavelength in a visible light region of CsI:T1 is 565 nm.

In the radiation detector 10 of the present embodiment, the conversion layer 14 is directly formed on the sensor substrate 12 as strip-shaped columnar crystals (not shown) by vapor-phase deposition methods, such as a vacuum vapor deposition method, a sputtering method, and a chemical vapor deposition (CVD) method. For example, in a case where CsI:T1 is used as the conversion layer 14, a vacuum vapor deposition method is used as a method of forming the conversion layer 14. In the vacuum vapor deposition method, CsI:Tl is heated and gasified by heating means, such as a resistance heating-type crucible in an environment with a vacuum degree of 0.01 Pa to 10 Pa, and CsI:T1 is deposited on the sensor substrate 12 with the temperature of the sensor substrate 12 as the room temperature (20° C.) to 300° C. As the thickness of the conversion layer 14, 100 μm to 800 μm is preferable.

Additionally, since the conversion layer 14 of the present embodiment is formed by the vapor-phase deposition methods as described above, as shown in FIG. 3, the thickness of the outer peripheral region of the conversion layer 14 tends to decrease toward the outside as seen as a whole. For that reason, the conversion layer 14 has an inclination such that the thickness thereof decreases toward the outside. In addition, in the present embodiment, as an example in which the thickness of the conversion layer 14 decreases toward the outer periphery, a form in which the conversion layer 14 has a constant inclination and the thickness gradually decreases is exemplified. However, the form of the conversion layer is not limited this form and may be, for example, a form in which the thickness changes stepwise.

Additionally, as shown in FIG. 3, the radiation detector 10 of the present embodiment comprises a pressure-sensitive adhesive layer 40, a reflective layer 42, an adhesive layer 44, and a protective layer 46. In addition, in the following, a direction in which the base material 11, the pixels 30, and the conversion layer 14 are lined up (upward-downward direction in FIG. 3) is referred to as a lamination direction (refer to FIG. 3, a lamination direction P). Additionally, for convenience of explanation, the conversion layer 14 side of the radiation detector 10 in the lamination direction P may be referred to as "upper", and the sensor substrate 12 side may be referred to as "lower".

As an example, as shown in FIG. 3, the pressure-sensitive adhesive layer 40 and the reflective layer 42 are provided on the entire conversion layer 14. Additionally, the pressure-sensitive adhesive layer 40 and the reflective layer 42 are not directly provided on the sensor substrate 12.

The pressure-sensitive adhesive layer 40 of the present embodiment is a light-transmitting layer, and examples of the material of the pressure-sensitive adhesive layer 40 include an acrylic pressure sensitive adhesive, a hot-melt pressure sensitive adhesive, and a silicone adhesive. Examples of the acrylic pressure sensitive adhesive include urethane acrylate, acrylic resin acrylate, epoxy acrylate, and the like. Examples of the hot-melt pressure sensitive adhesive include thermoplastics, such as ethylene-vinyl acetate copolymer resin (EVA), ethylene-acrylate copolymer resin (EAA), ethylene-ethyl acrylate copolymer resin (EEA), and ethylene-methyl methacrylate copolymer (EMMA).

As the thickness X of the pressure-sensitive adhesive layer 40 increases (that is, as the interval between the conversion layer 14 and the reflective layer 42 increases), the light converted by the conversion layer 14 is blurred within the pressure-sensitive adhesive layer 40. Therefore, the radiographic image obtained by the radiation detector 10 becomes a blurred image as a result. For that reason, as the thickness of the pressure-sensitive adhesive layer 40 increases, modulation transfer function (MTF) and detective quantum efficiency (DQE) decreases, and the degree of decrease also increases.

On the other hand, in a case where the thickness of the pressure-sensitive adhesive layer 40 is made too small, including a case where the pressure-sensitive adhesive layer 40 is not provided, there is a case where a minute air layer is formed between the conversion layer 14 and the reflective layer 42. In this case, the light directed from the conversion layer 14 to the reflective layer 42 is multiple-reflected between the air layer and the conversion layer 14 and between the air layer and the reflective layer 42. In a case where the light is attenuated by the multiple reflection, the sensitivity of the radiation detector 10 decreases. In a case where the thickness of the pressure-sensitive adhesive layer 40 exceeds 7 μm, the degree of decrease in DQE becomes larger and is lower than in a case where the pressure-sensitive adhesive layer 40 is not provided (in a case where the thickness is 0 μm). Additionally, in a case where the thickness of the pressure-sensitive adhesive layer 40 is less than 2 μm, the sensitivity of the radiation detector 10 decreases. Thus, in the present embodiment, the thickness of the pressure-sensitive adhesive layer 40 is set to 2 μm or more and 7 μm or less. In addition, the refractive index of the pressure-sensitive adhesive layer 40 is approximately 1.5, although the refractive index depends on the material.

In addition, the pressure-sensitive adhesive layer 40 has a function of fixing the reflective layer 42 to the conversion layer 14. However, in a case where the thickness of the pressure-sensitive adhesive layer 40 is 2 μm or more, it is possible to obtain a sufficient effect of suppressing the deviation of the reflective layer 42 in an in-plane direction (a direction intersecting the thickness direction) with respect to the conversion layer 14.

Meanwhile, as an example, as shown in FIG. 3, the reflective layer 42 is provided on the pressure-sensitive adhesive layer 40 and covers the entire upper surface of the pressure-sensitive adhesive layer 40 itself. The reflective layer 42 has a function of reflecting the light converted by the conversion layer 14.

As a material of the reflective layer 42, it is preferable to use an organic material, and it is preferable to use, for example, at least one of white polyethylene terephthalate (PET), $TiO_2$, $Al_2O_3$, foamed white PET, a polyester-based high-reflection sheet, specular reflection aluminum, or the like. Particularly, it is preferable to use the white PET as the material from a viewpoint of reflectivity.

In addition, the white PET is obtained by adding a white pigment, such as $TiO_2$ or barium sulfate, to PET. Additionally, the polyester-based high-reflection sheet is a sheet (film) having a multilayer structure in which a plurality of thin polyester sheets are laminated. Additionally, the foamed white PET is a white PET of which the surface is porous.

In the present embodiment, the thickness of the reflective layer 42 is 10 μm or more and 40 μm or less. In a case where the thickness of the reflective layer 42 is increased, there is a case where a level difference between an upper surface of an outer peripheral portion of the reflective layer 42 and an upper surface of the conversion layer 14 increases and at least one of the adhesive layer 44 or the protective layer 46 is lifted. Additionally, in a case where the thickness of the reflective layer 42 increases, a so-called stiffness state is brought about. Therefore, there is a case where bending does not occur easily along the inclination of the peripheral edge part of the conversion layer 14 and is not easily processed. For that reason, from these viewpoints, in the radiation detector 10 of the present embodiment, in a case where the white PET is used as the material of the reflective layer 42, the thickness of the reflective layer 42 is set to 40 μm or less as described above.

On the other hand, as the thickness of the reflective layer 42 decreases, reflectivity decreases. In a case where the reflectivity decreases, the image quality of a radiographic image to be obtained by the radiation detector 10 also tends to deteriorate. For that reason, from the viewpoint of the image quality of the radiographic image obtained by the radiation detector 10, it is preferable to set the lower limit of the thickness of the reflective layer 42 in consideration of a desired reflectivity (for example, 80%). In the radiation detector 10 of the present embodiment, in a case where the white PET is used as the material of the reflective layer 42, the thickness of the reflective layer 42 is set to 10 μm or more as described above.

Meanwhile, as an example, as shown in FIG. 3, the adhesive layer 44 is provided from above a region near an outer peripheral portion of the conversion layer 14 in the sensor substrate 12 to a region covering an end portion of the reflective layer 42. In other words, in the radiation detector 10 of the present embodiment, the adhesive layer 44 that covers the entire conversion layer 14 in which the pressure-sensitive adhesive layer 40 and the reflective layer 42 are provided is directly fixed (adhered) to the surface of the sensor substrate 12. The adhesive layer 44 has a function of fixing the reflective layer 42 to the sensor substrate 12 and the conversion layer 14. Additionally, the adhesive layer 44 has a function of fixing the protective layer 46. Examples of the material of the adhesive layer 44 include the same materials as the pressure-sensitive adhesive layer 40. In addition, in the present embodiment, the adhesive force of the adhesive layer 44 is stronger than the adhesive force of the pressure-sensitive adhesive layer 40.

Moreover, as an example, as shown in FIG. 3, the protective layer 46 is provided on the adhesive layer 44, and the protective layer 46 of the present embodiment covers the entire upper surface of the adhesive layer 44 that covers the conversion layer 14 in a state in which the upper surface thereof is covered with the pressure-sensitive adhesive layer 40 and the reflective layer 42. The protective layer 46 has a function of protecting the conversion layer 14 from moisture, such as humidity. Additionally, the protective layer 46 has a function of fixing the reflective layer 42 to the sensor substrate 12 and the conversion layer 14 together with the adhesive layer 44. Examples of the material of the protective layer 46 include organic films, and specifically include PET, polyphenylene sulfide (PPS), biaxially oriented polypropylene film (OPP), polyethylene naphthalate (PEN), PI, and the like. Additionally, as the protective layer 46, a laminated film of a resin film and a metal film may be used. Examples of the laminated film of the resin film and the metal film include an Alpet (registered trademark) sheet in which aluminum is laminated by causing an aluminum foil to adhere to an insulating sheet (film) such as polyethylene terephthalate.

Additionally, as shown in FIGS. 2 to 4, the flexible cable 406 is electrically connected to the first surface 11A of the base material 11 of the sensor substrate 12 via a terminal (not shown) such as an anisotropic conductive film. In addition, in the present embodiment, the term "connection" with respect to the flexible cables 206 and 406 means an electrical connection.

As in the example shown in FIGS. 3 and 4, one end of each of a plurality of (12 in FIG. 4) the flexible cables 406 is thermocompression-bonded to the sensor substrate 12. The flexible cable 406 has a function of connecting the signal processing unit 104 and the signal wiring line 36 (refer to FIG. 1) to each other. The plurality of signal lines (not shown) included in the flexible cable 406 are thermocompression-bonded to the sensor substrate 12 and thereby connected to the signal wiring line 36 (refer to FIG. 1). The flexible cable 406 of the present embodiment is an example of a first cable of the present disclosure.

On the other hand, the other end of the flexible cable 406 is thermocompression-bonded to the signal processing substrate 400. As an example, in the present embodiment, six flexible cables 406 are connected to one signal processing substrate 400. The plurality of signal lines (not shown) included in the flexible cable 406 are thermocompression-bonded to the signal processing substrate 400 and thereby connected to the circuits and elements (not shown) mounted on the signal processing substrate 400.

The signal processing substrate 400 of the present embodiment is a flexible printed circuit board (PCB) substrate, which is a so-called flexible substrate. Circuit components (not shown) mounted on the signal processing substrate 400 are components mainly used for processing analog signals (hereinafter referred to as "analog components"). Specific examples of the analog components include charge amplifiers, analog-to-digital converters (ADCs), digital-to-analog converters (DAC), and power source ICs. Additionally, the circuit components of the present embodiment also include coils around a power source, which has a relatively large component size, and large-capacity smoothing capacitors. In addition, the signal processing substrate 400 may not necessarily a flexible substrate and may be a non-flexible rigid substrate or a rigid flexible substrate.

Additionally, a signal processing integrated circuit (IC) 404 is mounted on the flexible cable 406. The signal processing IC 404 is connected to a plurality of signal lines (not shown) included in the flexible cable 406.

In the present embodiment, the signal processing unit 104 is realized by the signal processing substrate 400 and the signal processing IC 404 mounted on the flexible cable 406. The signal processing IC 404 is an IC including a circuit different from the analog components mounted on the signal processing substrate 400 among various circuits and elements that realize the signal processing unit 104. The signal processing IC 404 of the present embodiment is an example of a signal processing circuit of the present disclosure.

Meanwhile, as shown in FIGS. 2 to 4, the flexible cable 206 is electrically connected to the side of the first surface 11A of the base material 11 of the sensor substrate 12 that intersects the side to which the flexible cable 406 is connected, via a terminal (not shown) such as an anisotropic conductive film.

As in the example shown in FIGS. 2 and 4, one end of each of a plurality of (12 in FIGS. 2 and 4) the flexible cables 206 is thermocompression-bonded to the sensor substrate 12. The flexible cable 206 has a function of connecting the drive unit 102 and the scanning wiring line 38 (refer to FIG. 1). A plurality of signal lines (not shown) included in the flexible cable 206 are thermocompression-bonded to the sensor substrate 12 and thereby connected to the scanning wiring line 38 (refer to FIG. 1). The flexible cable 206 of the present embodiment is an example of a second cable of the present disclosure.

On the other hand, the other end of the flexible cable 206 is thermocompression-bonded to the driving substrate 200. As an example, in the present embodiment, six flexible cables 206 are connected to one driving substrate 200. The plurality of signal lines (not shown) included in the flexible cable 206 are thermocompression-bonded to the driving substrate 200 and thereby connect to circuits and elements (not shown) mounted on the driving substrate 200.

Similarly to the signal processing substrate 400, the driving substrate 200 of the present embodiment is a flexible printed circuit board (PCB) substrate, which is a so-called flexible substrate. Additionally, similarly to the signal processing substrate 400, circuit components (not shown) mounted on the driving substrate 200 are components mainly used for processing digital signals (hereinafter, referred to as "digital components"). Digital components tend to have a relatively smaller area (size) than analog components to be described below. Specific examples of the digital components include digital buffers, bypass capacitors, pull-up/pull-down resistors, damping resistors, electromagnetic compatibility (EMC) countermeasure chip components, power source ICs, and the like. In addition, the driving substrate 200 may not be necessarily a flexible substrate and may be a non-flexible rigid substrate or a rigid flexible substrate.

Additionally, a driving IC 204 is mounted on the flexible cable 206 at a position near the sensor substrate 12. The driving IC 204 is connected to the plurality of signal lines (not shown) included in the flexible cable 206.

In the present embodiment, the drive unit 102 is realized by the driving substrate 200 and the driving IC 204 mounted on the flexible cable 206. The driving IC 204 is an IC including, among various circuits and elements that realize the drive unit 102, a circuit different from the digital components mounted on the driving substrate 200. The driving IC 204 of the present embodiment is an example of a drive circuit of the present disclosure.

Additionally, as shown in FIGS. 2 to 4, the driving substrate 200 and the signal processing substrate 400 of the present embodiment are provided on the same side of the sensor substrate 12. For that reason, the flexible cable 206 of the present embodiment has a shape bent in a direction intersecting the side to which the flexible cable 206 is connected from a direction in which the flexible cable 206 is connected to the side of the sensor substrate 12. In other words, as shown in FIG. 4, the flexible cable 206 includes a portion that includes one end connected to the sensor substrate 12 and extends in a first direction a intersecting the direction of the side of the sensor substrate 12 to which the flexible cable 206 is connected, and a portion that includes the other end connected to the driving substrate 200 and extends in a second direction β that intersects the first direction. As an example, in the present embodiment, as shown in FIGS. 2 and 4, each of the flexible cables 206 shows an L-shape bent by about 90 degrees. By forming each of the flexible cables 206 in an L-shape in this way, the flexible cables 206 do not intersect with each other. Therefore, the flexible cable 206 is less susceptible to electromagnetic induction and noise.

By gently folding the flexible cable 206 toward the first surface 11A, as shown in FIGS. 2 and 3, the flexible cable 206 passes over the first surface 11A side of the base material 11 of the sensor substrate 12, more specifically, the conversion layer 14 and is connected to the driving substrate 200.

In addition, in order to prevent the flexible cable 206 from being reflected in the radiographic image generated by the radiation detector 10, the flexible cable 206 is folded to a side opposite to a side where the radiation detector 10 is irradiated with radiation. In other words, the flexible cable 206 passes through a side opposite to the side irradiated with the radiation out of the conversion layer 14 (first surface 11A) side of the sensor substrate 12 and the second surface 11B side of the base material 11 in the sensor substrate 12.

Figure 5:
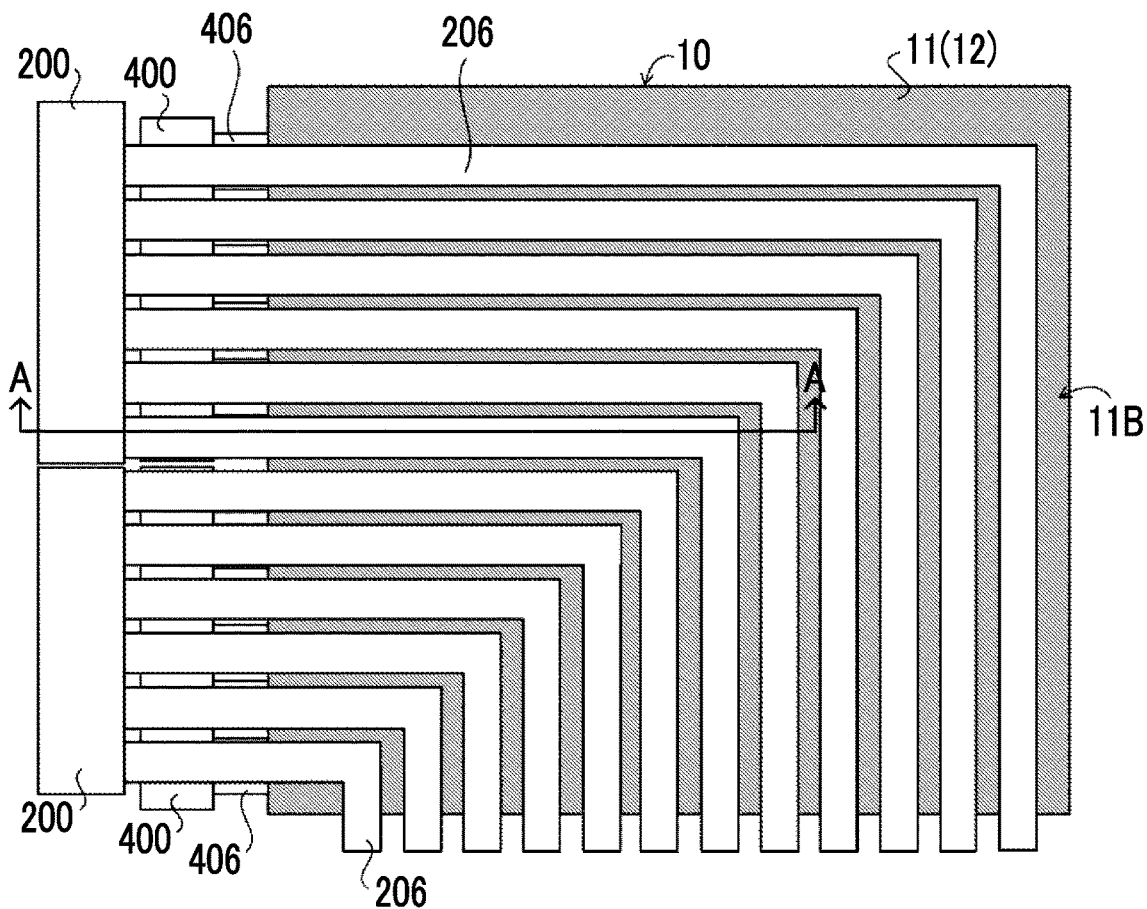
FIG. 5 is a plan view of another example of the radiographic imaging apparatus of the first embodiment as seen from a second surface side of a base material in a sensor substrate.
Figure 6:
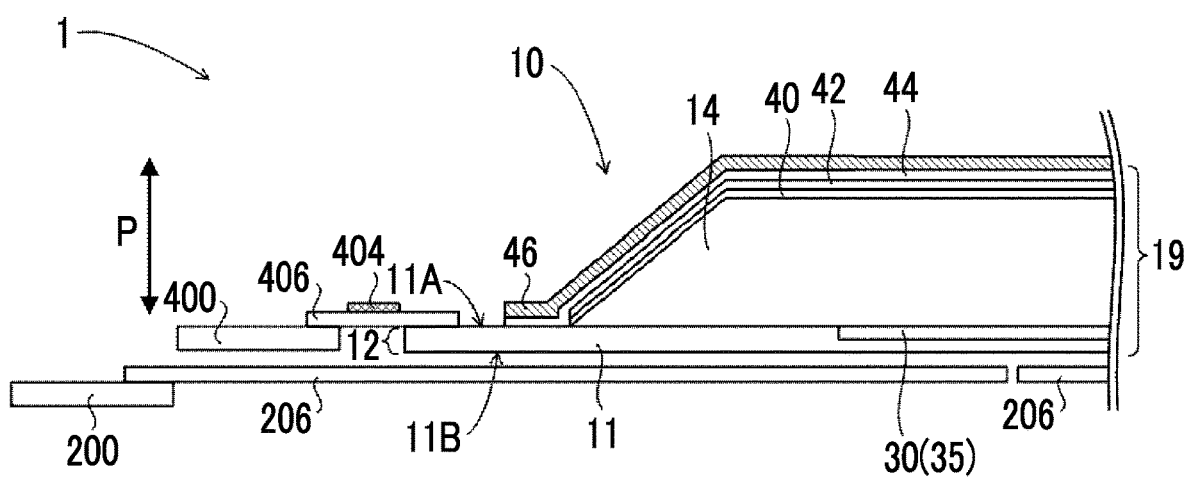
FIG. 6 is a cross-sectional view taken along line A-A of the radiographic imaging apparatus shown in FIG. 5.

Specifically, in the case of the ISS type in which radiation is emitted from the second surface 11B side of the base material 11 as in the radiation detector 10 of the present embodiment, the flexible cable 206 passes through the conversion layer 14 side as shown in FIGS. 2 and 3. On the other hand, in the case of the penetration side sampling (PSS) type in which radiation is emitted from the conversion layer 14 side, the flexible cable 206 passes through the second surface 11B side of the base material 11 of the sensor substrate 12 as shown in FIGS. 5, and FIG. 6 that is a cross-sectional view taken along line A-A of FIG. 5.

In addition, the radiographic imaging apparatus 1 according to the present embodiment may have, for example, the forms shown in the following Modification Examples 1-1 to 1-3.

Modification Example 1-1

Figure 7:
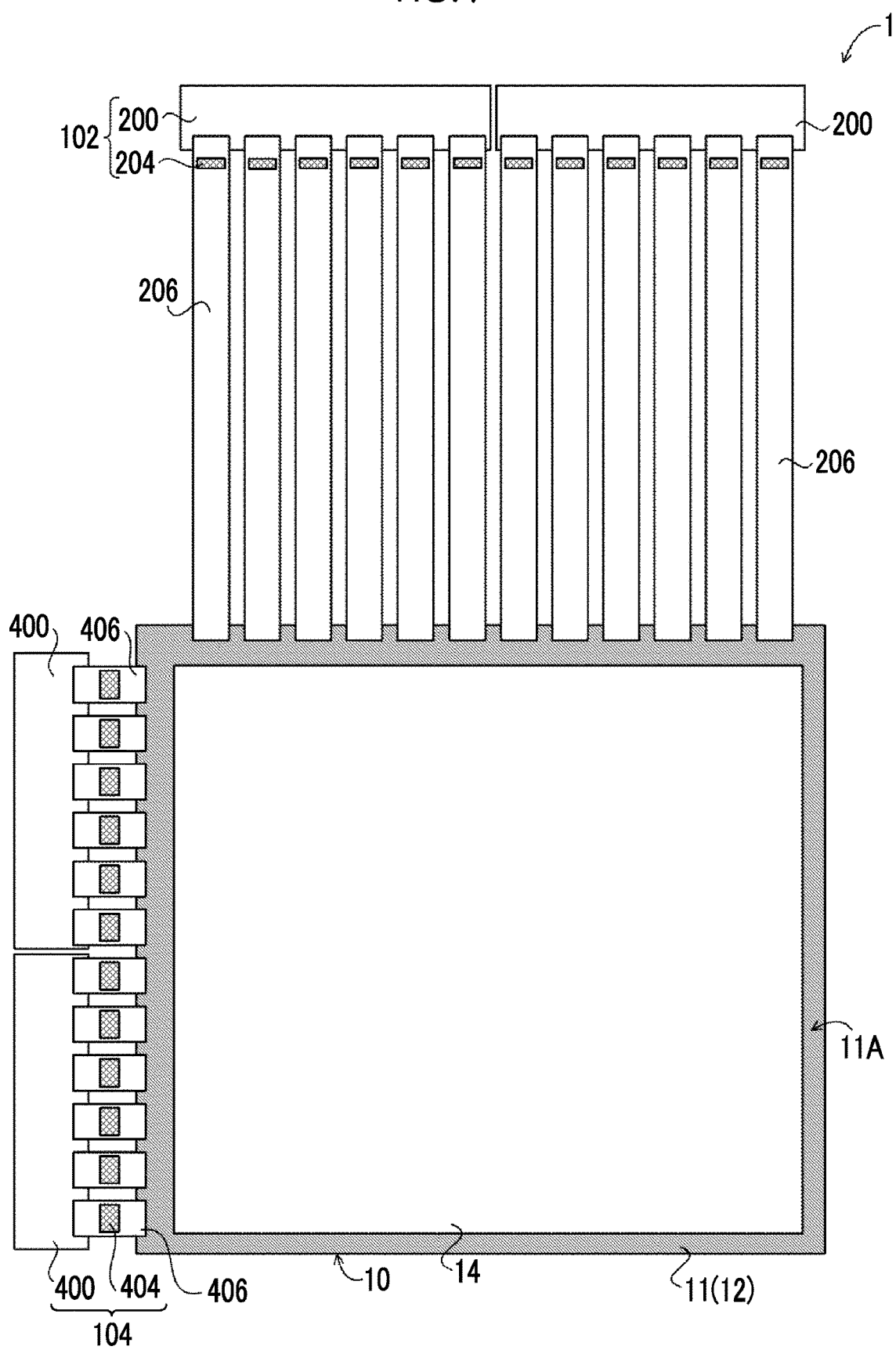
FIG. 7 is a plan view showing an example of a state in which the flexible cable in the radiographic imaging apparatus of Modification Example 1-1 is unfolded without being folded.
Figure 8:
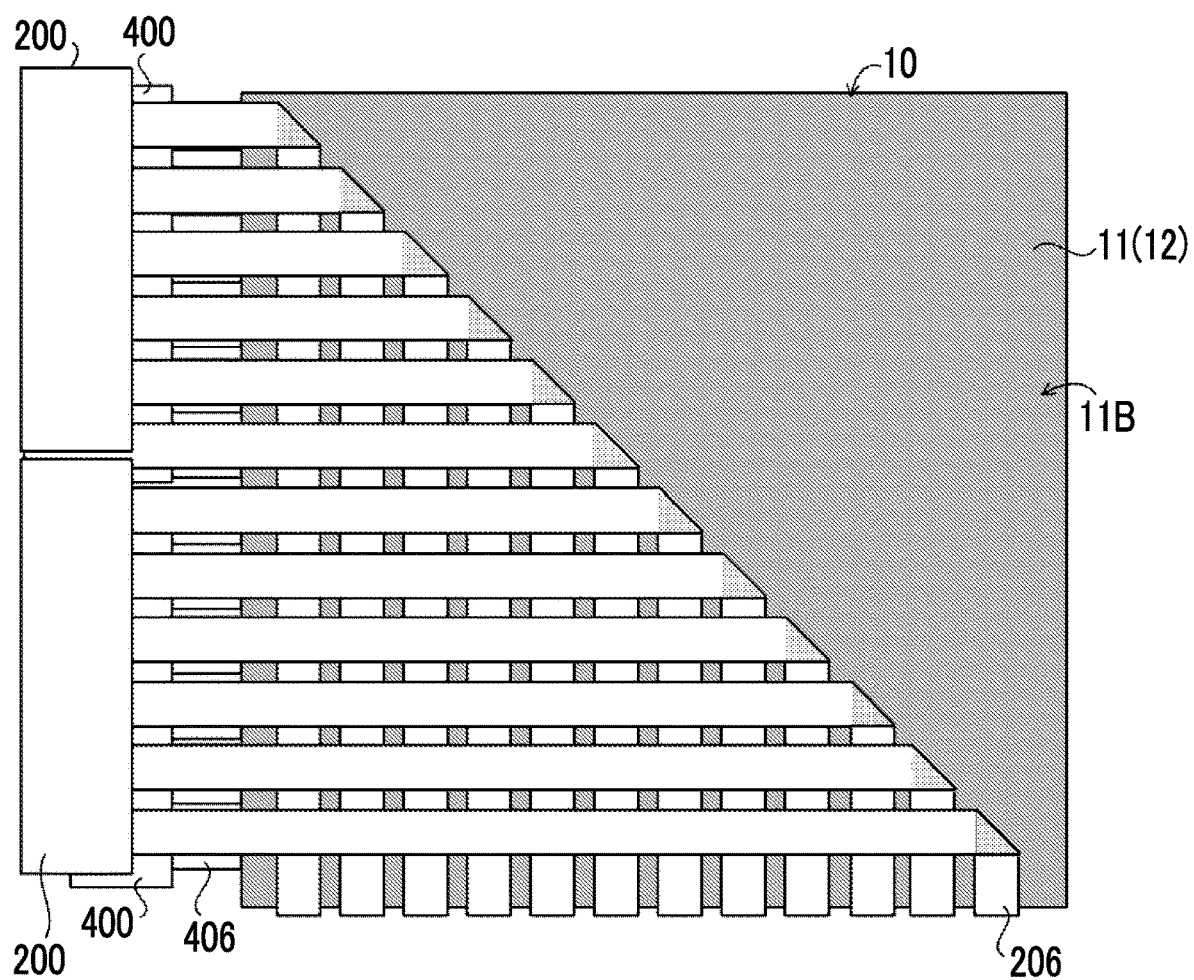
FIG. 8 is a plan view of the radiographic imaging apparatus of Modification Example 1-1 as seen from the second surface side of the base material.

As shown in FIG. 7, the flexible cable 206 of the radiographic imaging apparatus 1 may have a straight shape extending in a straight line. FIG. 8 shows an example in a state in which the radiographic imaging apparatus 1 is of the PSS type and the flexible cable 206 is folded toward the second surface 11B of the base material 11 in the sensor substrate 12. As shown in FIG. 8, the flexible cable 206 is bent in a direction in which the flexible cable 206 is folded with each other an extending direction of the flexible cable 206, and further bent in a direction intersecting the extending direction of the flexible cable 206.

As shown in FIG. 7, in the present modification example, the plurality of flexible cables 206 connected to the sensor substrate 12 all have the same shape. For that reason, the radiographic imaging apparatus 1 can be easily manufactured, and the manufacturing cost can be suppressed.

Figure 9:
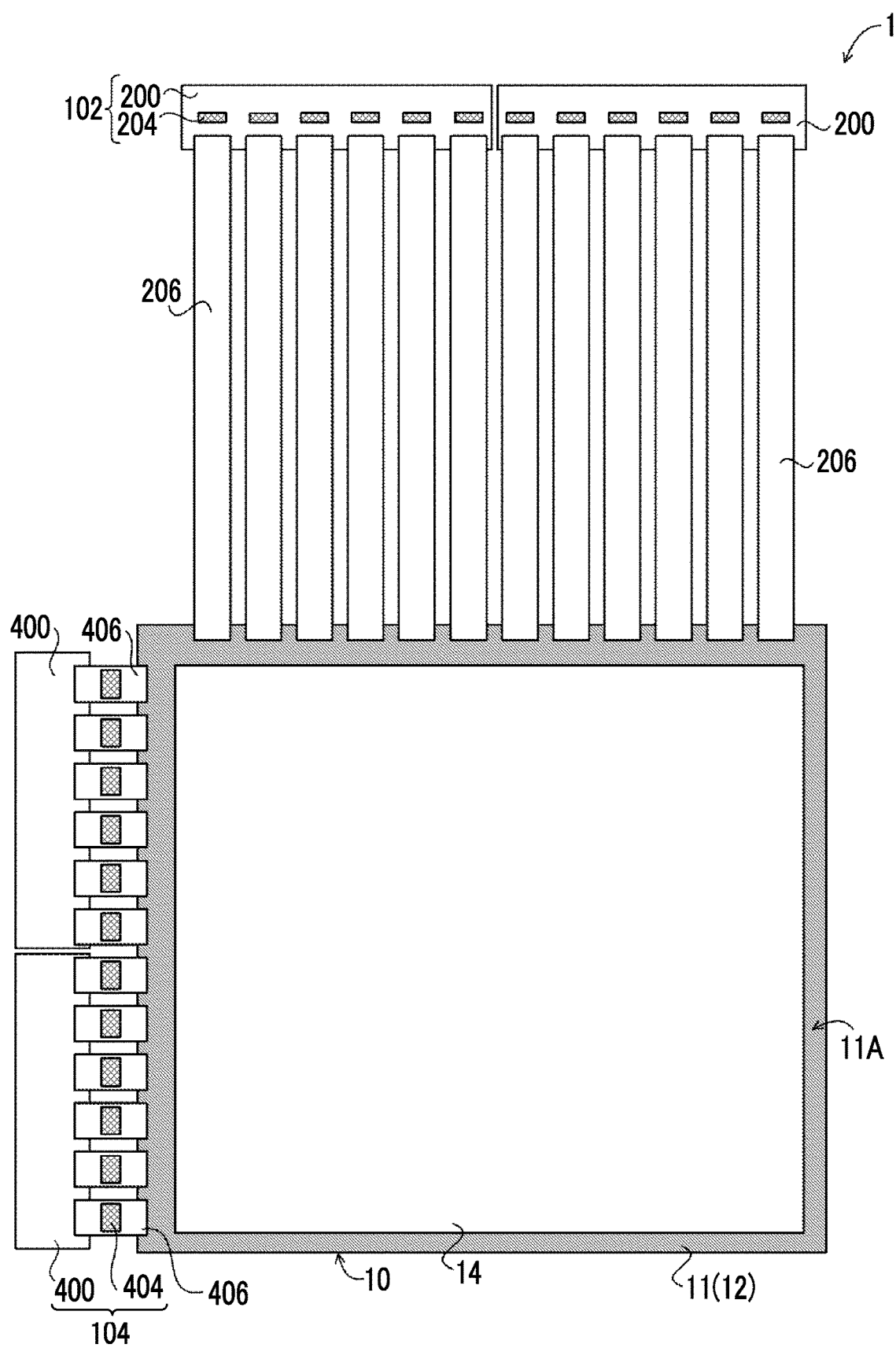
FIG. 9 is a plan view showing another example of a state in which the flexible cable in the radiographic imaging apparatus of Modification Example 1-1 is unfolded without being folded.

Additionally, in the radiographic imaging apparatus 1 of the modification example shown in FIG. 7, the driving IC 204 is mounted on the side of the flexible cable 206 close to the driving substrate 200. In this way, the position where the driving IC 204 is mounted is not limited. For example, as shown in FIG. 9, a form may be adopted in which the driving IC 204 is mounted on the driving substrate 200. The specific position where the driving IC 204 is mounted may be, for example, a position according to the influence of noise due to the driving IC 204, the specifications of the radiographic imaging apparatus 1, the size of the housing 120 (refer to FIG. 29) that houses the radiation detector 10 and the like, and the like.

Modification Example 1-2

Figure 10:
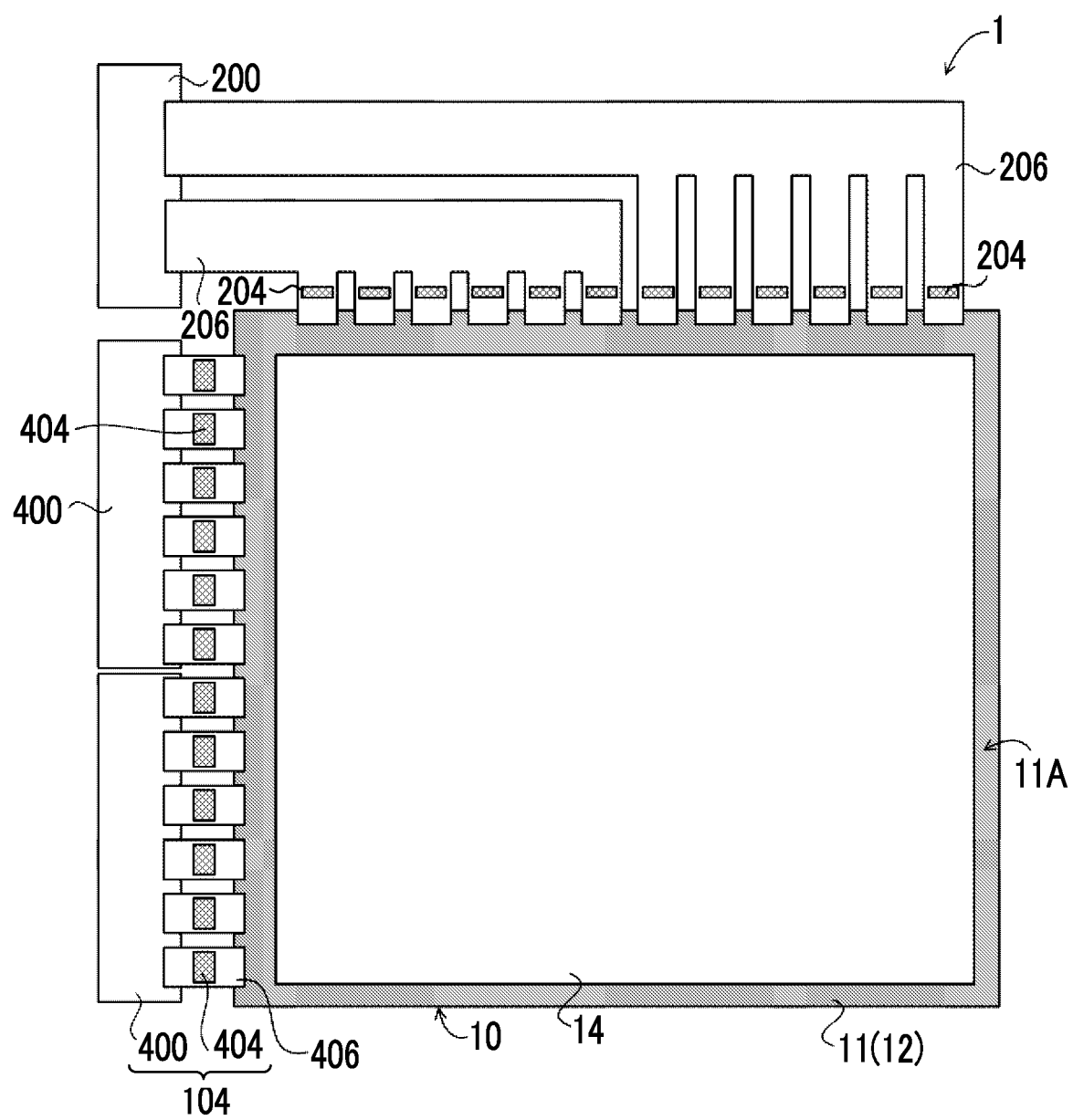
FIG. 10 is a plan view of an example of the radiographic imaging apparatus of Modification Example 1-2 as seen from the second surface side of the base material.

As shown in FIG. 10, a form may be adopted in which the number of flexible cables 206 of the radiographic imaging apparatus 1 connected to the driving substrate 200 is smaller than the number of flexible cable 206 connected to the sensor substrate 12. In the example shown in FIG. 10, a relatively wide end portion of the flexible cable 206 connected to the driving substrate 200 are divided into six, and each of the six-divided end portions is connected to the sensor substrate 12. Additionally, the driving IC 204 is mounted on each of the six end portions of the flexible cable 206 connected to the sensor substrate 12.

Compared with the flexible cables 206 (refer to FIG. 4) of the radiographic imaging apparatus 1 of the above embodiment, there is a difference in that the plurality of flexible cables 206 (six in FIG. 10) in the flexible cable 206 are integrated into one and connected to the driving substrate 200.

By integrating the plurality of flexible cables 206 in this way, the flexible cables 206 are easily handled in the radiographic imaging apparatus 1 of the present modification example.

Modification Example 1-3

Figure 11:
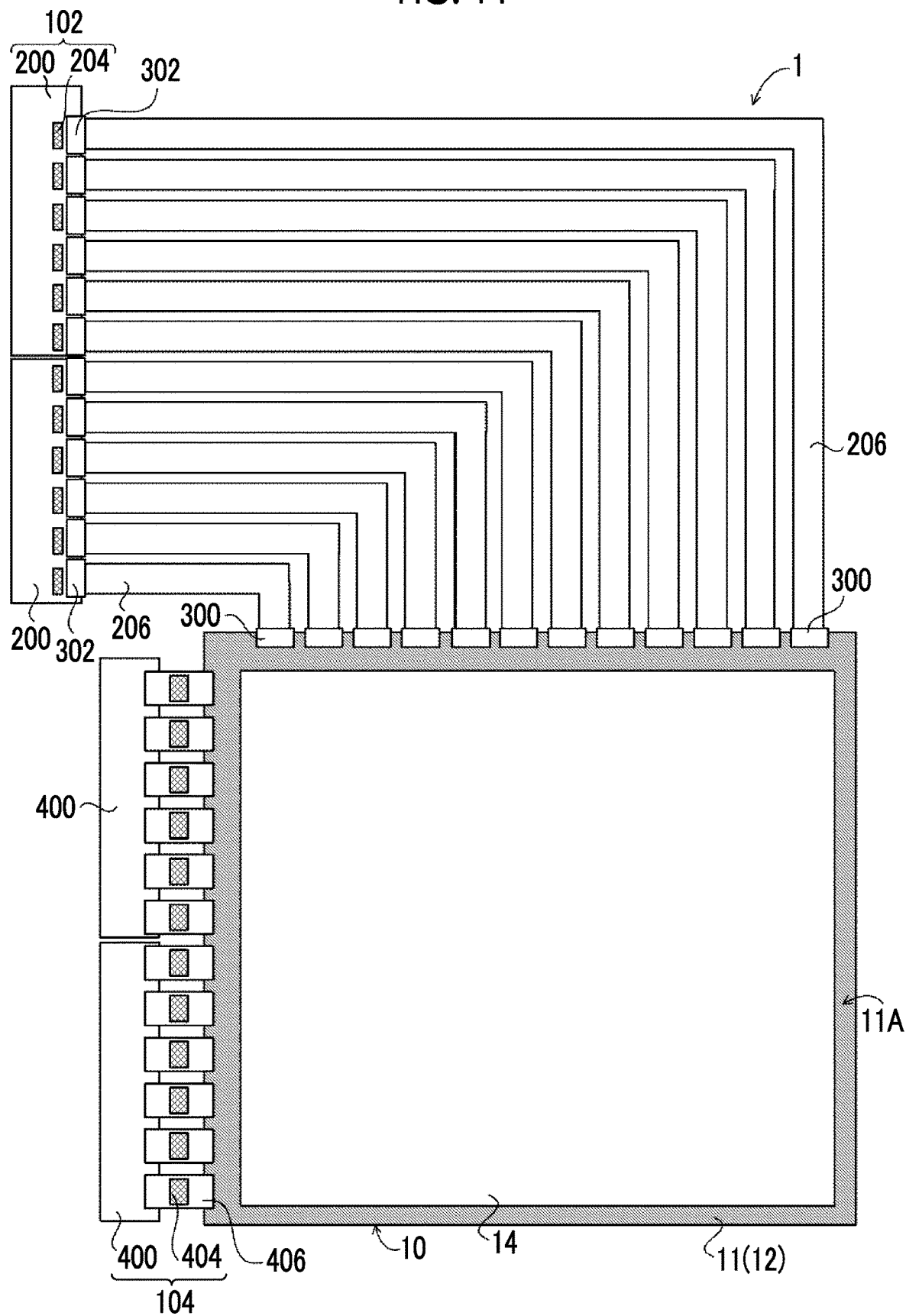
FIG. 11 is a plan view of an example of the radiographic imaging apparatus of Modification Example 1-3 as seen from the second surface side of the base material.

As shown in FIG. 11, a form may be adopted in which the flexible cable 206 of the radiographic imaging apparatus 1 is connected to the scanning wiring line 38 of the sensor substrate 12 via a connector 300 instead of being connected to the sensor substrate 12 by the thermocompression bonding. Additionally, a form may be adopted in which the flexible cable 206 is connected to the driving substrate 200 via a connector 302 instead of being connected to the driving substrate 200 by the thermocompression bonding. Examples of such connector 300 and 302 include a zero insertion force (ZIF) structure connector and a Non-ZIF structure connector.

In this way, by performing at least one of the connection between the flexible cable 206 and the sensor substrate 12 or the connection between the flexible cable 206 and the driving substrate 200 with each of the connectors 300 and 302, in the radiographic imaging apparatus 1 of the present modification example, the flexible cable 206 is easily handled even in a case where the flexible cable 206 becomes long.

In this way, in the radiographic imaging apparatus 1 of the present embodiment, the flexible cable 206 connected to the sensor substrate 12 passes through the first surface 11A side of the base material 11 or the second surface 11B side opposite to the first surface 11A of the base material 11 and is electrically connected to the driving substrate 200. Accordingly, the driving substrate 200 can be disposed on the same side of the sensor substrate 12 as the signal processing substrate 400.

Therefore, according to the radiographic imaging apparatus 1 of the present embodiment, a portion corresponding to the sensor substrate 12 can be made thinner.

Second Embodiment

Figure 12:
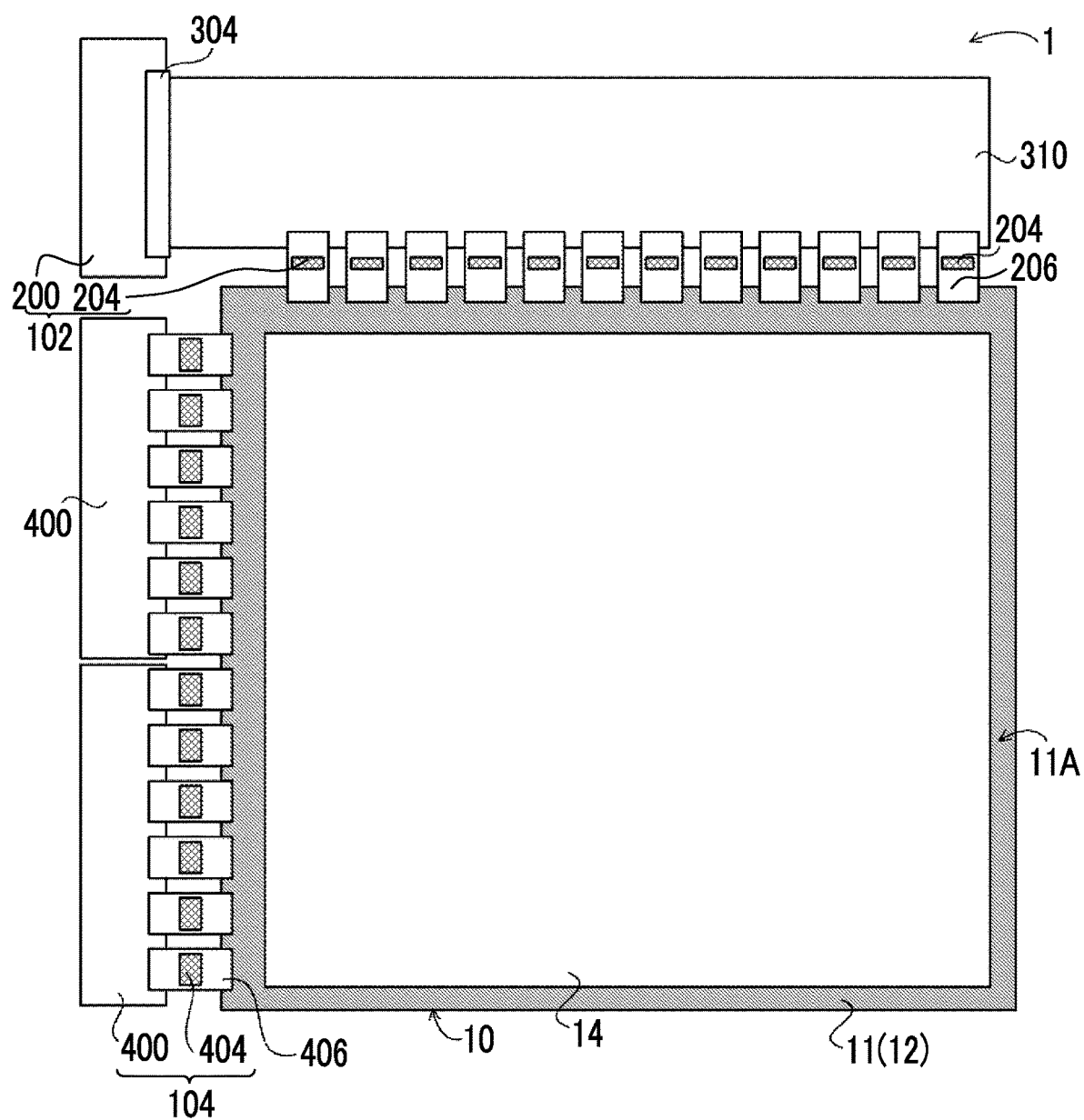
FIG. 12 is a plan view of an example of a radiographic imaging apparatus according to a second embodiment as seen from the second surface side of the base material.

Next, a second embodiment will be described. FIG. 12 is a plan view of the radiographic imaging apparatus 1 of the present embodiment in a state in which the flexible cable 206 is not folded, as seen from the first surface 11A side of the base material 11.

The flexible cable 206 of the present embodiment is different from the radiographic imaging apparatus 1 (refer to FIG. 4) of the first embodiment in that an end portion opposite to an end portion connected to the sensor substrate 12 is connected to a relay substrate 310 instead of the driving substrate 200. As an example, in the present embodiment, the relay substrate 310 and the flexible cable 206 are connected to each other by thermocompression bonding. Additionally, the relay substrate 310 and the driving substrate 200 are connected to each other by a connector 304.

In addition, in the example shown in FIG. 12, one relay substrate 310 is shown, but the number of relay substrates 310 is not limited to one. For example, as in an example shown in FIG. 13, the radiographic imaging apparatus 1 may have a form in which two relay substrates 310 (310A and 310B) are used. In the example shown in FIG. 13, six flexible cables 206 are connected to the relay substrate 310A in order from the side closest to the signal processing substrate 400, and the relay substrate 310A and the driving substrate 200 are connected to each other by a connector 304A. Additionally, six flexible cables 206 are connected to the relay substrate 310B in order from the side far from the signal processing substrate 400, and the relay substrate 310B and the driving substrate 200 are connected to each other by a connector 304B.

Figure 14:
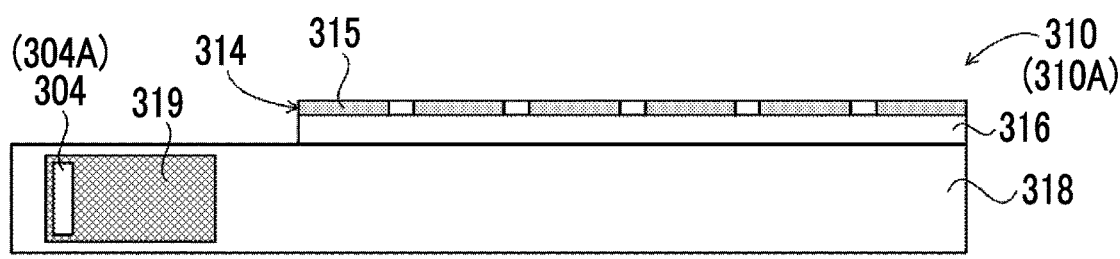
FIG. 14 is a plan view showing an example of a relay substrate.

The structure of the relay substrate 310 of the present embodiment will be described with reference to FIG. 14. In addition, although the relay substrate 310A is shown as a specific example in FIG. 14, since the basic structure of the relay substrate 310 of the present embodiment is the same, the relay substrate 310 will be described here. As shown in FIG. 14, the relay substrate 310 of the present embodiment includes three portions, a connecting portion 314, a folding portion 316, and a relay portion 318.

The connecting portion 314 is a multi-layer flexible printed circuit (FPC), and as an example, in the present embodiment, a four-layer FPC is used. The connecting portion 314 is provided with a thermocompression bonding pattern 315 to which the flexible cable 206 is thermocompression-bonded.

Additionally, the folding portion 316 is a portion for folding the relay substrate 310 toward the first surface 11A side or the second surface 11B side of the base material 11 and is thinner than the connecting portion 314 and the relay portion 318. As an example, in the present embodiment, by using a single-layer FPC as the folding portion 316, the thickness of the folding portion 316 is reduced to ¼ (quarter) as compared to each of the connecting portion 314 and the relay portion 318.

Additionally, the relay portion 318 is a portion for relaying the connection between the flexible cable 206 and the driving substrate 200, and a component mounting region 319 on which the above digital components mounted on the driving substrate 200 are mounted is provided on the side where the connector 304 connected to the driving substrate 200 is provided. The relay portion 318 is a multi-layer FPC, and as an example, in the present embodiment, a 4-layer FPC is used.

In addition, in the present embodiment, a flexible (having flexibility) substrate is used as the relay substrate 310, but the present invention is not limited to the present embodiment, and a rigid substrate or a rigid flexible substrate may be used as the relay substrate 310 that relays the flexible cable 206 and the driving substrate 200.

In addition, the radiographic imaging apparatus 1 according to the present embodiment may have, for example, forms shown in the following Modification Examples 2-1-1 to 2-2-2.

Modification Example 2-1-1

Figure 15:
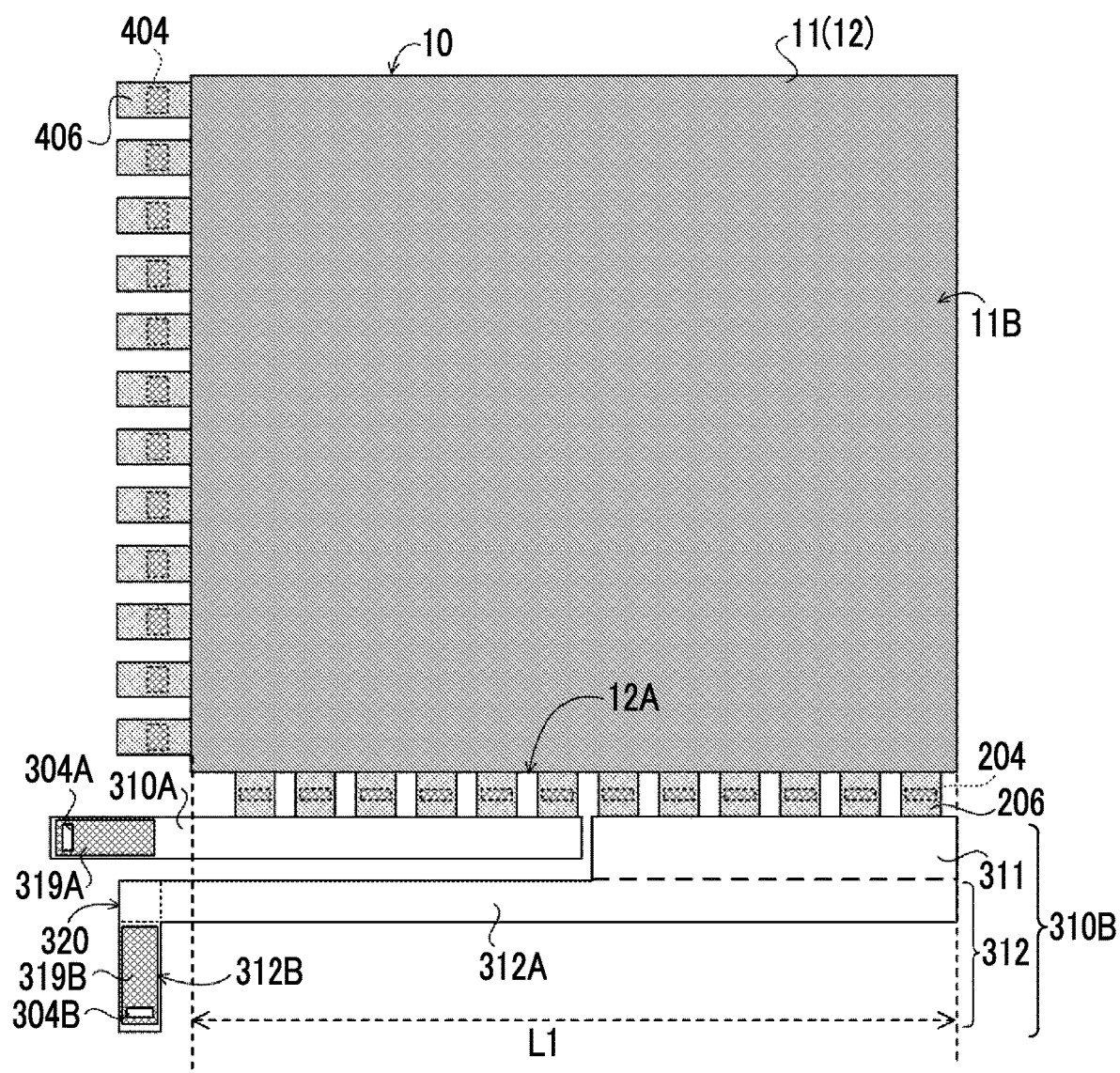
FIG. 15 is a plan view of an example of the radiographic imaging apparatus of Modification Example 2-1-1 as seen from the second surface side of the base material.

FIG. 15 shows a modification example of the relay substrates 310A and 310B. FIG. 15 shows a plan view of the radiographic imaging apparatus 1 of the present modification example as seen from the second surface 11B side of the base material 11. In addition, in FIG. 15, the description of the driving substrate 200, the signal processing substrate 400, and the like is omitted in order to avoid complicating the drawings. In the relay substrate 310A in the radiographic imaging apparatus 1 of the present modification example, similarly to the relay substrate 310A described with reference to FIG. 14, a component mounting region 319A on which the digital components mounted on the driving substrate 200 are mounted and a connector 304A are provided on the side where the connector 304 connected to the driving substrate 200 is provided.

Figure 16:
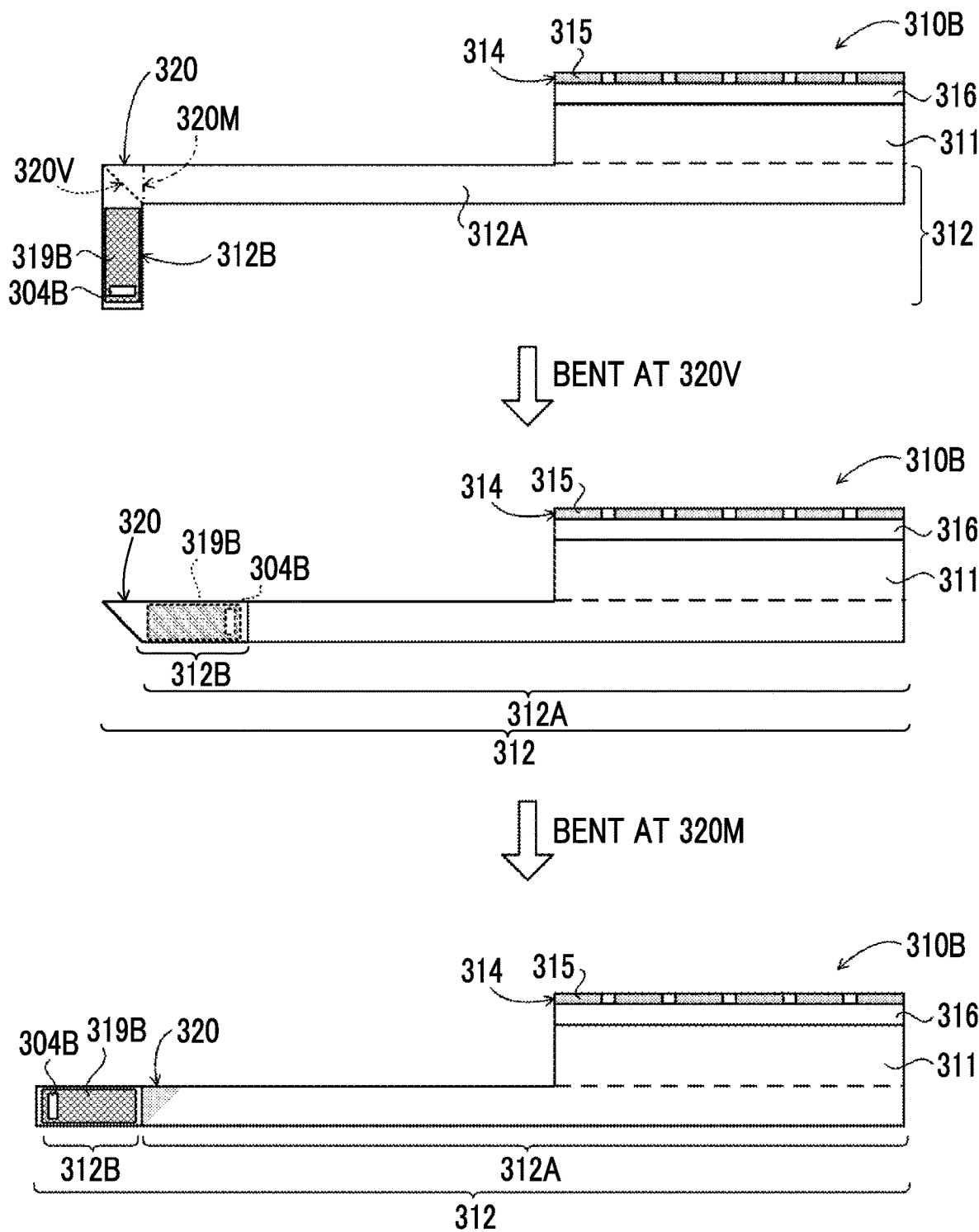
FIG. 16 is a diagram for explaining an example of bending a second relay portion of Modification Example 2-1-1.

Meanwhile, as shown in FIGS. 15 and 16, the relay substrate 310B includes a first relay portion 311 electrically connected to the flexible cable 206, and a second relay portion 312. The second relay portion 312 shows an L-shape having a long side 312A that extends along a side 12A of the sensor substrate 12 to which the flexible cable 206 is electrically connected, and a short side 312B that extends in a direction intersecting the direction in which the long side 312A extends and is electrically connected to the driving substrate 200. The short side 312B is provided with a component mounting region 319B on which the digital components mounted on the driving substrate 200 are mounted, and a connector 304B.

The long side 312A and the short side 312B of the second relay portion 312 intersect each other by a bending portion 320, and the short side 312B is bent at the bending portion 320 in the direction along the long side 312A. The bending of the second relay portion 312 will be described with reference to FIG. 16. First, the short side 312B is bent in a state where the short side 312B overlaps the long side 312A by a valley bending line 320V of the bending portion 320. Next, the short side 312B is bent in a direction in which the tip is separated from the long side 312A by a mountain bending line 320M of the bending portion 320. As an example, in the present embodiment, an overlap region where the second relay portion 312 overlaps by bending the bending portion 320 is set to a position that does not overlap the component mounting region 319B, and is set to a position that overlaps the long side 312A.

By bending the second relay portion 312 in this way, the length of the second relay portion 312 extending along the side 12A of the sensor substrate 12 becomes longer than the length of the long side 312A.

Figure 17:
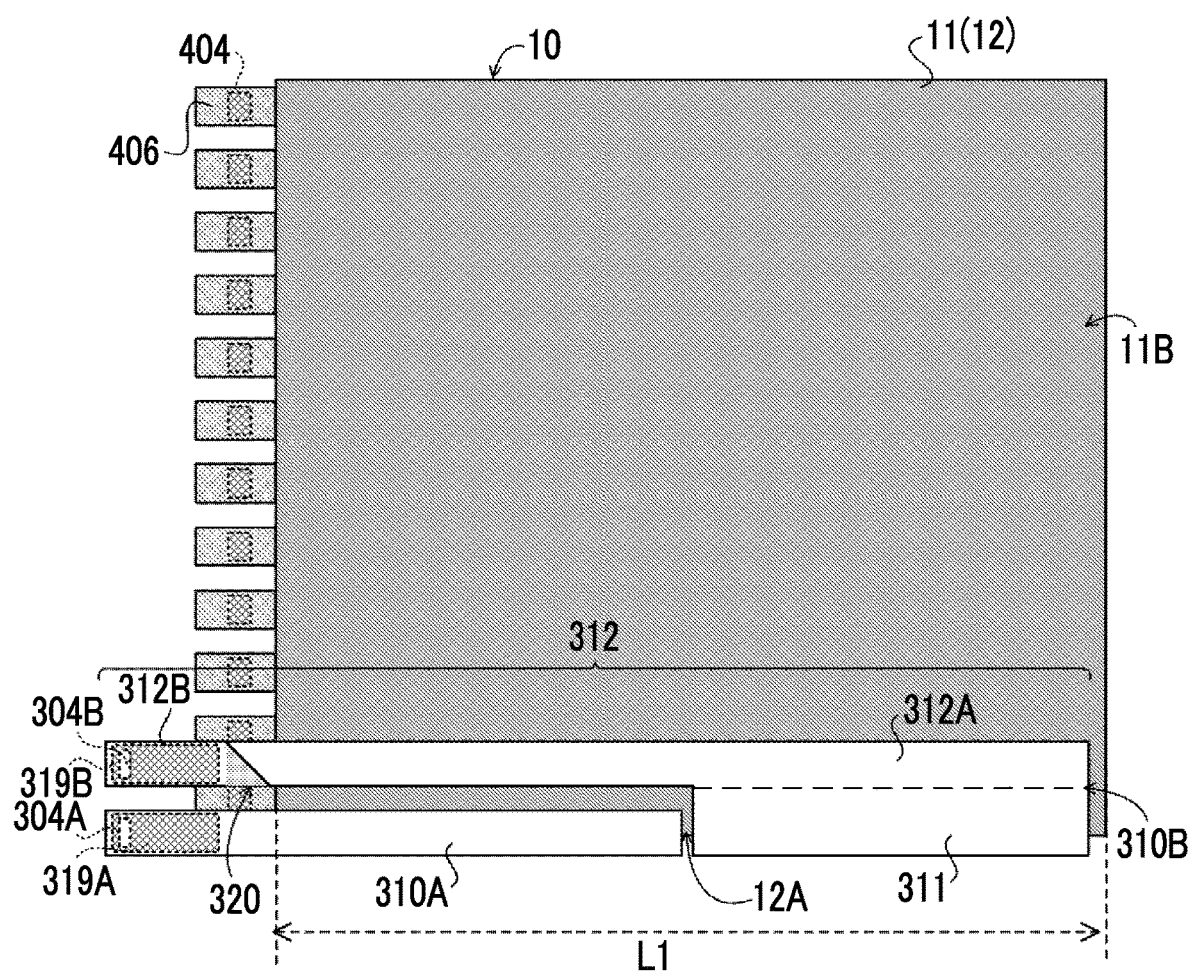
FIG. 17 is a plan view of an example of the radiographic imaging apparatus of Modification Example 2-1-1 as seen from the second surface side of the base material.

FIG. 17 shows an example of a state in which the relay substrates 310A and 310B are folded toward the second surface 11B of the base material 11 in the sensor substrate 12 in the radiographic imaging apparatus 1 of the present modification example. In addition, in FIG. 17, the description of the driving substrate 200, the flexible cable 206, the signal processing substrate 400, and the like is omitted in order to avoid complicating the drawings.

As shown in FIG. 17, the bending portion 320 is located outside the sensor substrate 12, and the bending portion 320 and the sensor substrate 12 do not overlap each other. Additionally, the component mounting region 319B of the second relay portion 312 is also located outside the sensor substrate 12, and the component mounting region 319B and the sensor substrate 12 do not overlap each other.

In this way, in the present modification example, in order to bend the short side 312B of the second relay portion 312 in the direction along the long side 312A, the length of the second relay portion 312 extending along the side 12A of the sensor substrate 12 can be made longer than the long side 312A. For that reason, even in a case where the length of the long side 312A is about a length L1 of the side 12A of the sensor substrate 12 or less than the length L1, the length of the second relay portion 312 along the side 12A can be made longer than the length L1 of the side 12A. For that reason, the driving substrate 200 can be disposed at a position that does not overlap the sensor substrate 12. Additionally, according to the present modification example, since the size (length) of a substrate constituting the relay substrate 310B can be suppressed, the manufacturing suitability can be improved, and the increase in cost resulting from the increase in size can be suppressed.

Additionally, according to the radiographic imaging apparatus 1 of the present modification example, the overlap region generated by bending the bending portion 320 of the relay substrate 310B does not overlap the sensor substrate 12. Therefore, the portion of the radiographic imaging apparatus 1 corresponding to the sensor substrate 12 can be made thinner.

In addition, in the relay substrate 310B, the direction in which the long side 312A and the short side 312B intersect each other is not limited to the form of the present modification example. For example, an L-shaped form opposite to that of the present modification example may be, specifically, a form in which the short side 312B extends toward the first relay portion 311. Additionally, the "L-shape" referred to in the relay substrate 310B is not limited to the form in which the long side 312A and the short side 312B intersect each other at a right angle, and also includes a form in which the long side 312A and the short side 312B intersect each other at a right angle.

Additionally, the method of bending the relay substrate 310B in the bending portion 320 is not limited. For example, bending using a mountain bending line as the above-described valley bending line 320V and using a valley bending line as the mountain bending line 320M may be performed. Additionally, the position of the overlap region of the second relay portion 312 by bending the bending portion 320 is not limited as long as the position of the overlap region is a position that does not overlap the sensor substrate 12 but is preferably a position where the portion that overlaps the component mounting region 319B is small, and more preferably a position that does not overlap the component mounting region 319B as described above.

Modification Example 2-1-2

Figure 18:
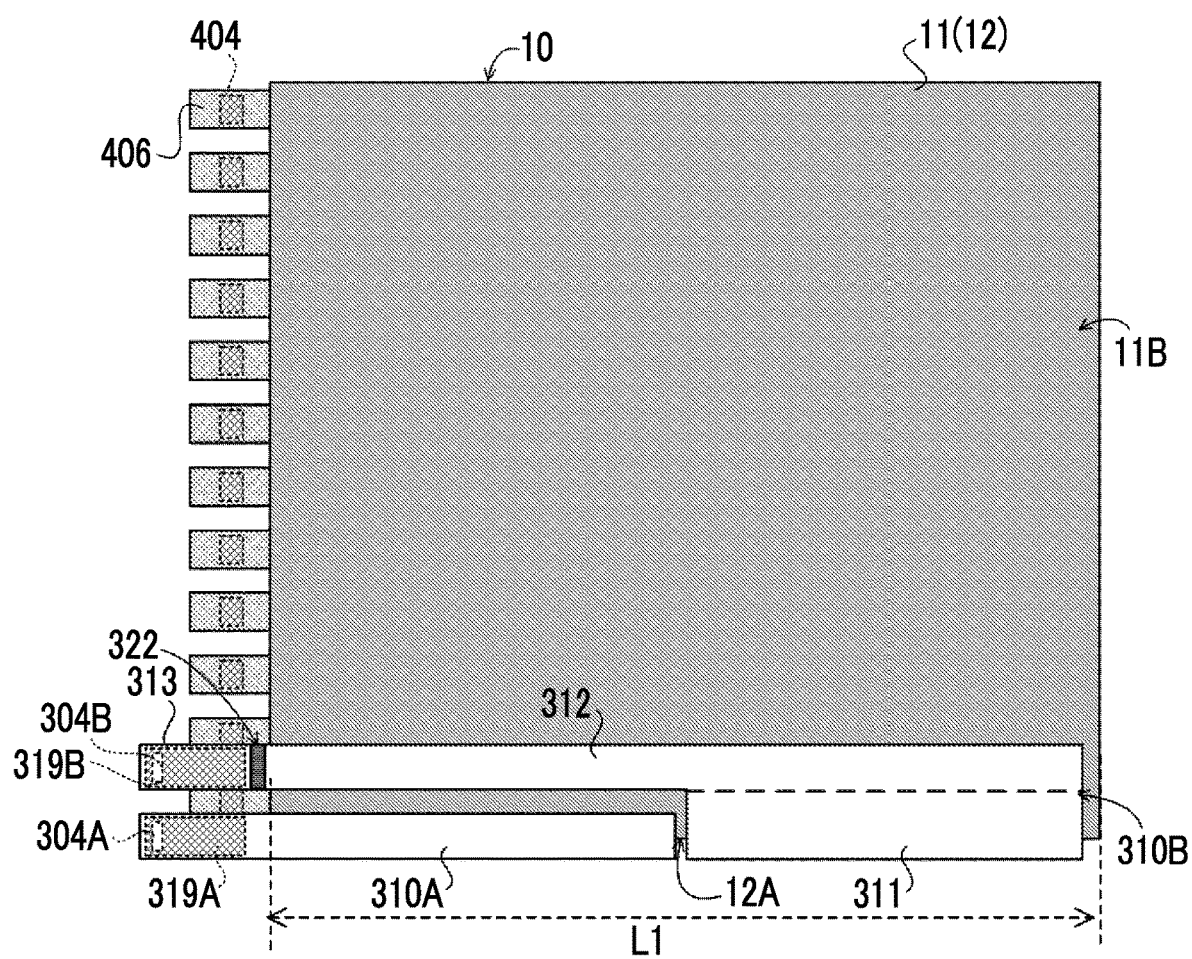
FIG. 18 is a plan view of an example of the radiographic imaging apparatus of Modification Example 2-1-2 as seen from the second surface side of the base material.

FIG. 18 shows an example of a state in which the relay substrates 310A and 310B are folded toward the second surface 11B of the base material 11 in the sensor substrate 12 in the radiographic imaging apparatus 1 of the present modification example. In addition, in FIG. 18, the description of the driving substrate 200, the flexible cable 206, the signal processing substrate 400, and the like is omitted in order to avoid complicating the drawings.

As shown in FIG. 18, since the relay substrate 310A of the present modification example is the same as the relay substrate 310A of Modification Example 2-1-1, the description thereof will be omitted.

Figure 19:
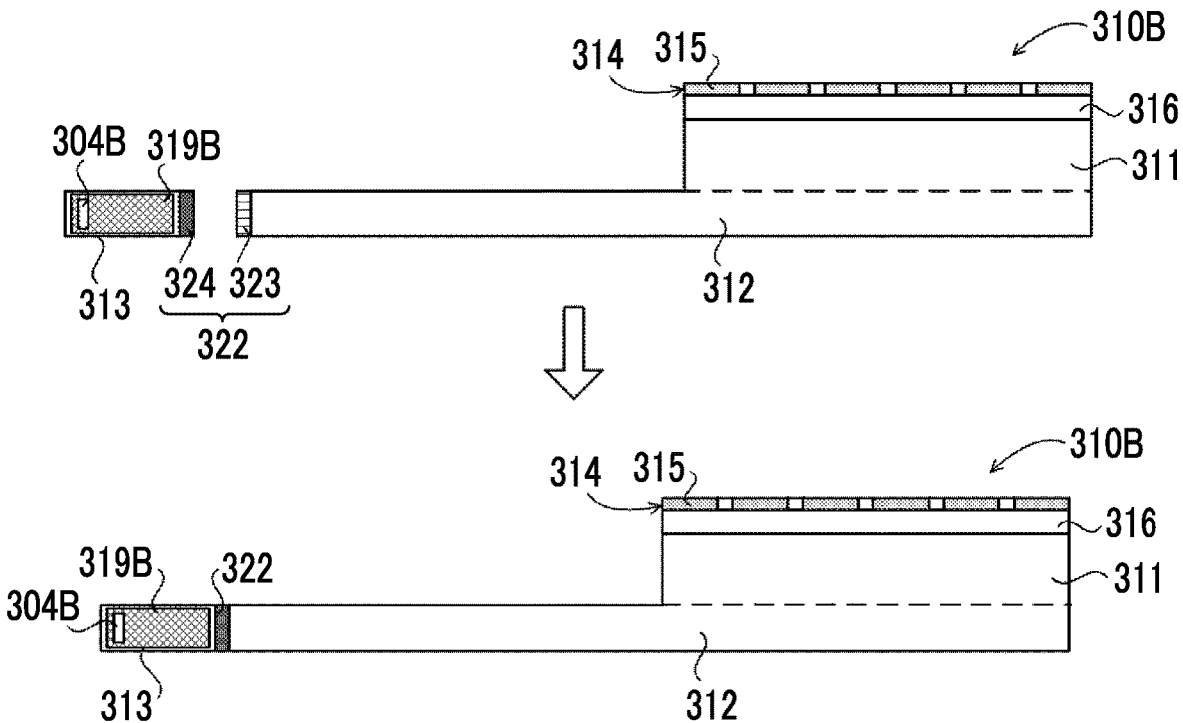
FIG. 19 is a view for explaining an example of the connection between the second relay portion and a third relay portion 313 of Modification Example 2-1-2.

On the other hand, as shown in FIGS. 18 and 19, the relay substrate 310B of the present modification example includes the first relay portion 311 electrically connected to the flexible cable 206, the second relay portion 312, and a third relay portion 313. The second relay portion 312 extends along the side 12A of the sensor substrate 12 to which the flexible cable 206 is electrically connected. The third relay portion 313 has one end electrically connected to an end portion of the second relay portion 312 and the other end electrically connected to the driving substrate 200. The third relay portion 313 is provided with a component mounting region 319B on which the digital components mounted on the driving substrate 200 are mounted and the connector 304B.

Specifically, as shown in FIG. 19, as the second relay portion 312 and the third relay portion 313 are thermocompression-bonded to each other by a connecting portion 322 including a thermocompression bonding pattern 323 of the second relay portion 312 and a thermocompression bonding pattern 324 of the third relay portion 313, the second relay portion 312 and the third relay portion 313 are electrically connected to each other. In addition, in the thermocompression bonding between the second relay portion 312 and the third relay portion 313, the top and bottom (front and back) of the thermocompression bonding pattern 323 of the second relay portion 312 and the thermocompression bonding pattern 324 of the third relay portion 313 are not limited. As an example, in the present modification example, the second relay portion 312 and the third relay portion 313 are thermocompression-bonded to each other in a state in which the thermocompression bonding pattern 323 is located on an upper (front) side in FIG. 19 and the thermocompression bonding pattern 324 is located on the lower (back) side.

As shown in FIG. 18, the connecting portion 322 is provided in a region that does not overlap the sensor substrate 12. Additionally, the connecting portion 322 of the present modification example is provided at a position that does not overlap the signal processing IC 404.

In this way, since the relay substrate 310B includes the second relay portion 312 and the third relay portion 313 connected to the second relay portion 312, the length of the relay substrate 310B extending along the side 12A of the sensor substrate 12 can be longer than the side 12A.

For that reason, even in a case where the length of the second relay portion 312 extending along the side 12A of the sensor substrate 12 is about the length L1 of the side 12A or less than the length L1, the length of the relay substrate 310B along the side 12A can be made longer than the length L1 of the side 12A. For that reason, the driving substrate 200 can be disposed at a position that does not overlap the sensor substrate 12. Additionally, according to the present modification example, since the size (length) of a substrate constituting the relay substrate 310B can be suppressed, the manufacturing suitability can be improved, and the increase in cost resulting from the increase in size can be suppressed.

Additionally, according to the radiographic imaging apparatus 1 of the present modification example, since the connecting portion 322 does not overlap the sensor substrate 12, the portion of the radiographic imaging apparatus 1 corresponding to the sensor substrate 12 can be made thinner.

Figure 20:
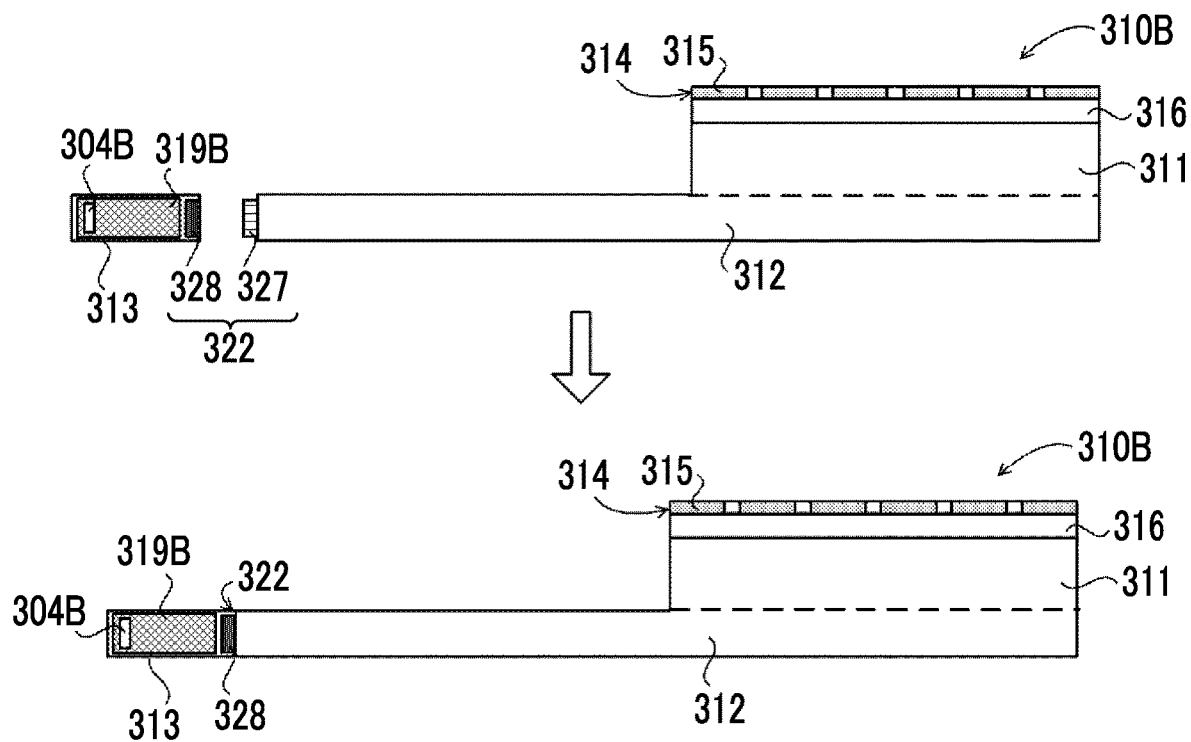
FIG. 20 is a view for explaining another example of the connection between the second relay portion and the third relay portion 313 of Modification Example 2-1-2.

In addition, the configuration of the connecting portion 322 is not limited to the form of the present modification example. An example of another form of the connecting portion 322 is shown in FIG. 20. The connecting portion 322 shown in FIG. 20 includes a connector connection pattern 327 provided in the second relay portion 312 and a connector 328 provided in the third relay portion 313. In the connecting portion 322 shown in FIG. 20, by connecting (inserting) the connector connection pattern 327 to the connector 328, the second relay portion 312 and the third relay portion 313 are electrically connected to each other via the connector 328.

Additionally, in the present modification example, a configuration in which the relay substrate 310B includes the second relay portion 312 and the third relay portion 313 and the second relay portion 312 and the third relay portion 313 are electrically connected by the connecting portion 322 has been described. However, the present invention is not limited to the present form, and the relay substrate 310A may also have the same form. That is, as the relay substrate 310A has a form including the second relay portion 312 and the third relay portion 313, and the second relay portion 312 and the third relay portion 313 are electrically connected to each other by the connecting portion 322, the length of the relay substrate 310A along the side 12A of the sensor substrate 12 may be longer than that of the second relay portion 312.

Modification Example 2-2-1

Figure 21:
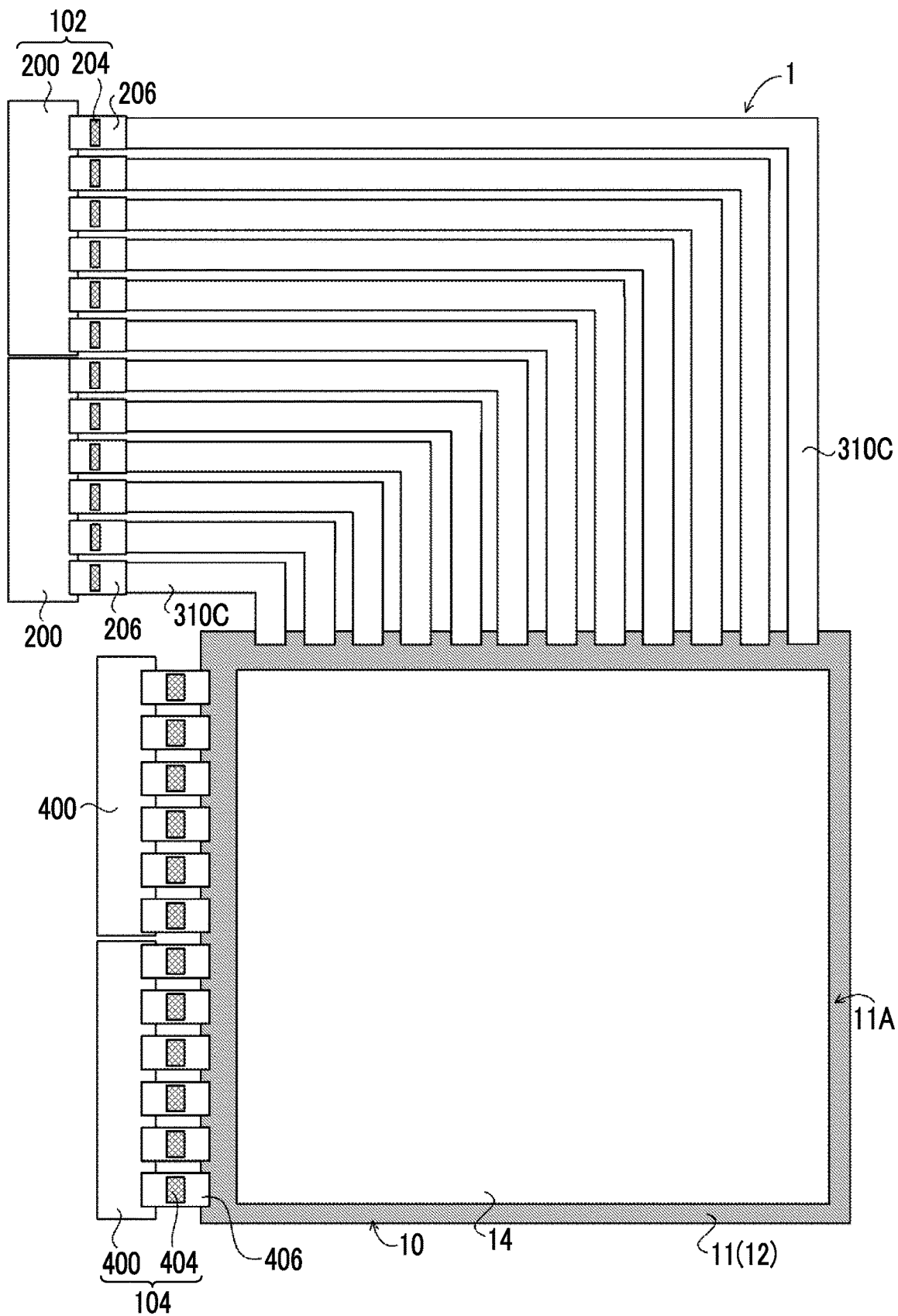
FIG. 21 is a plan view of an example of the radiographic imaging apparatus of Modification Example 2 as seen from the second surface side of the base material.
Figure 22:
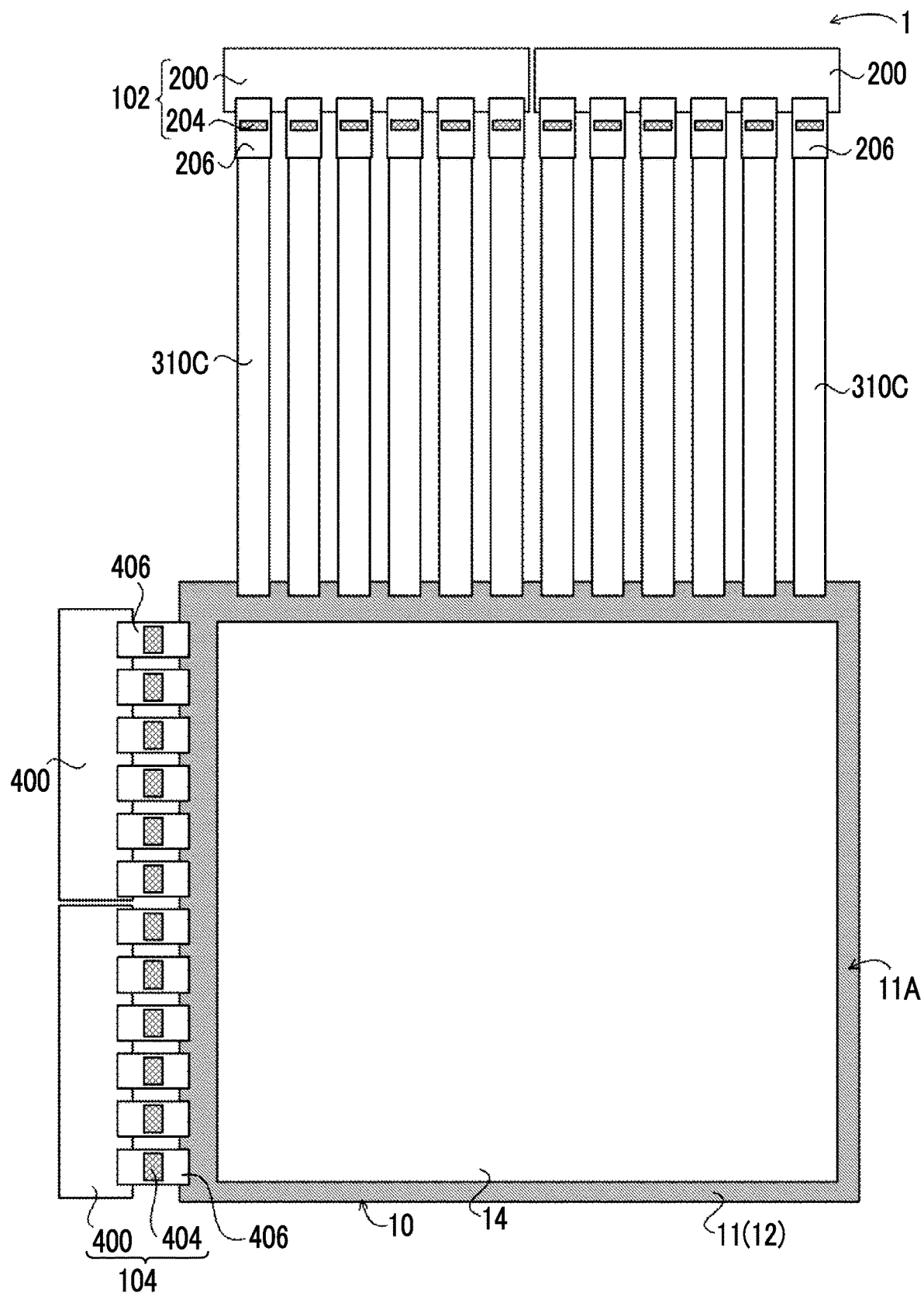
FIG. 22 is a plan view of another example of the radiographic imaging apparatus of Modification Example 2-2-1 as seen from the second surface side of the base material.

As shown in FIGS. 21 and 22, the radiographic imaging apparatus 1 may have a form in which the end portion of the flexible cable 206 is connected to the relay substrate 310C instead of the sensor substrate 12. As shown in FIGS. 21 and 22, the radiographic imaging apparatus 1 of the present modification example comprises a plurality of relay substrates 310C (12 in FIG. 21), and one end of each relay substrate 310C is connected to the flexible cable 206 by thermocompression bonding, and the other end thereof is connected to the sensor substrate 12 by thermocompression bonding.

In the example shown in FIG. 21, each of the relay substrates 310C has an L-shape that is bent about 90 degrees in the direction of the driving substrate 200 (signal processing substrate 400), similarly to the flexible cable 206 (refer to FIG. 4) of the first embodiment. Additionally, in the example shown in FIG. 22, each of the relay substrates 310C has a straight shape that extends in a straight line, similarly to the flexible cable 206 of Modification Example 1-1 (refer to FIG. 7) of the first embodiment.

As in the radiographic imaging apparatus 1 of the present modification example shown in FIGS. 21 and 22, a form may be adopted in which the flexible cable 206 and the sensor substrate 12 are connected to each other by the relay substrate 310C.

Modification Example 2-2-2

Figure 23:
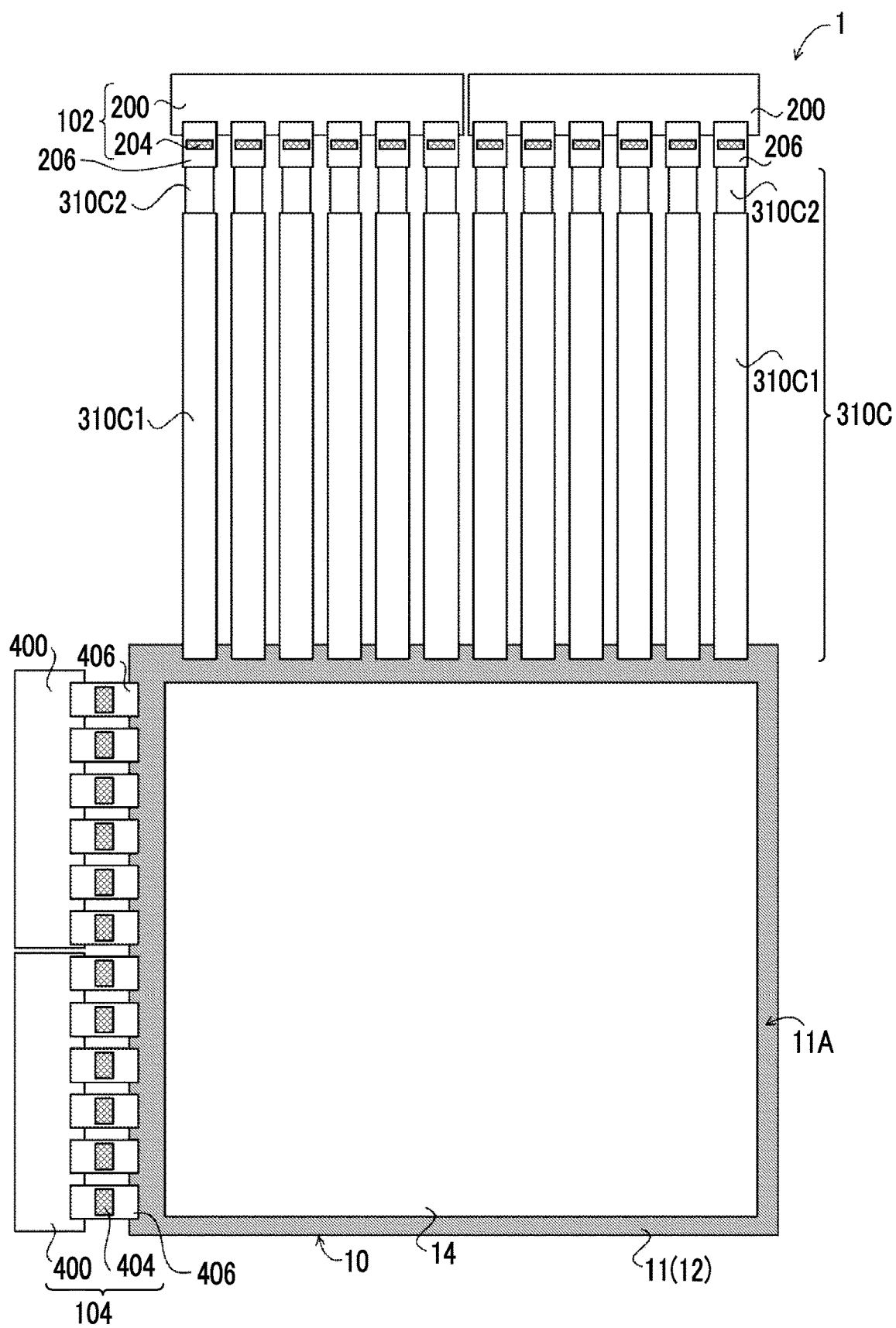
FIG. 23 is a plan view of an example of the radiographic imaging apparatus of Modification Example 2-2-2 as seen from the first surface side of the base material.

The relay substrate 310 of the radiographic imaging apparatus 1 may include a plurality of relay substrates. FIG. 23 shows a plan view of the radiographic imaging apparatus 1 in a form in which the relay substrate 310C includes two relay substrates, as seen from the first surface 11A side of the base material 11.

The relay substrate 310C of the radiographic imaging apparatus 1 shown in FIG. 23 includes a first relay substrate 310C1 and a second relay substrate 310C2. One end of the first relay substrate 310C1 is electrically connected to the sensor substrate 12. One end of the second relay substrate 310C2 is electrically connected to the other end of the first relay substrate 310C1, and the other end thereof is electrically connected to the flexible cable 206. As an example, in the present modification example, the second relay substrate 310C2 and each of the first relay substrate 310C1 and of the flexible cable 206 are electrically connected to each other by thermocompression bonding.

Figure 24:
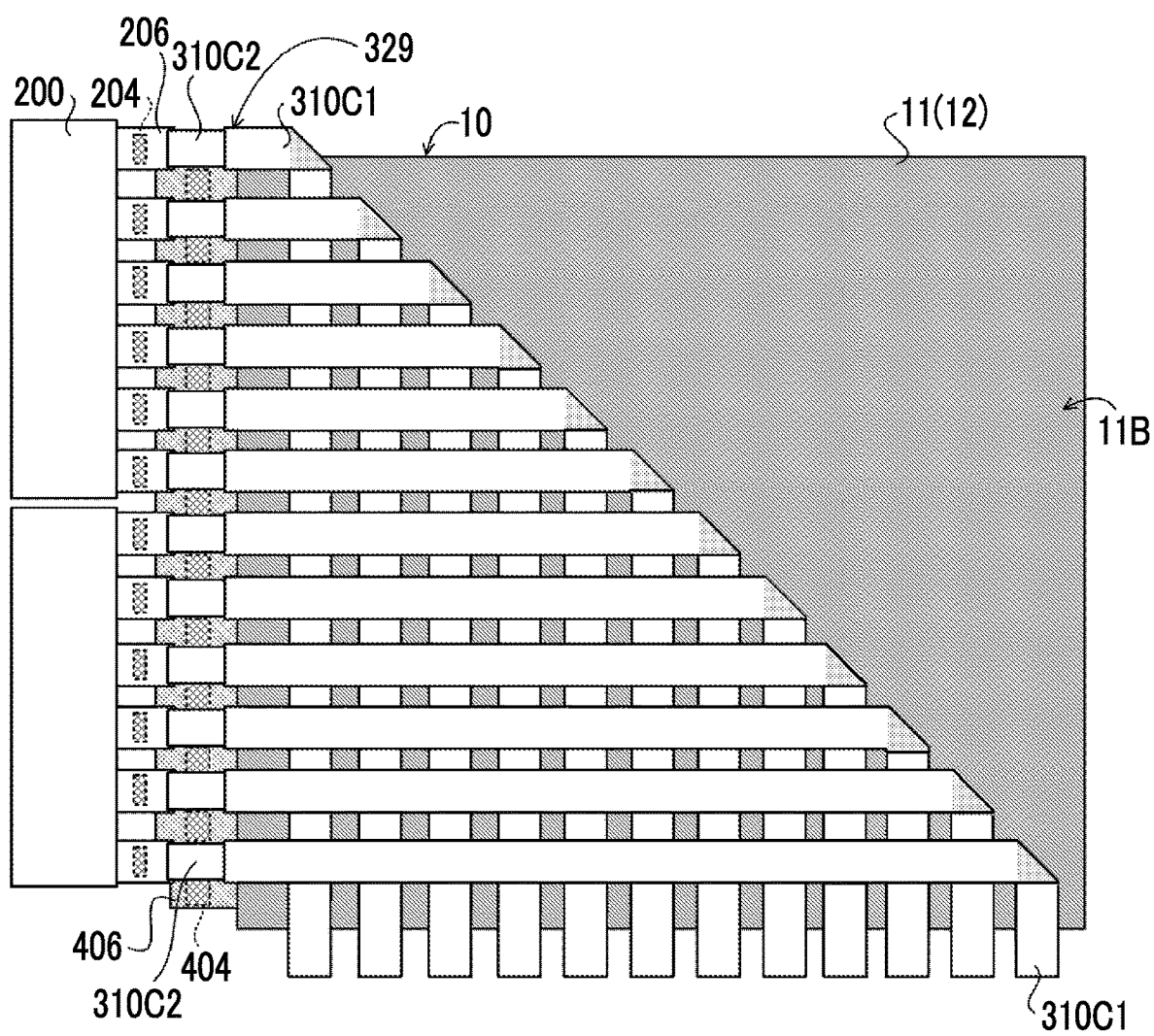
FIG. 24 is a plan view of the radiographic imaging apparatus of Modification Example 2-2-2 as seen from the second surface side of the base material.

FIG. 24 shows an example of a state in which the relay substrate 310C is folded toward the second surface 11B of the base material 11 on the sensor substrate 12. As shown in FIG. 24, the first relay substrate 310C1 is bent in the direction in which the first relay substrate 310C is folded with each other the extending direction of the first relay substrate 310C1, and further bent in the direction intersecting the extending direction of the first relay substrate 310C1.

Additionally, as shown in FIG. 24, a connecting portion 329 by which the first relay substrate 310C1 and the second relay substrate 310C2 are electrically connected is located outside the sensor substrate 12 is located outside the sensor substrate 12, and the connecting portion 329 and the sensor substrate 12 do not overlap each other.

In this way, since the relay substrate 310C includes the first relay substrate 310C1 and the second relay substrate 310C2, according to the radiographic imaging apparatus 1 of the present modification example, the size (length) of each of the first relay substrate 310C1 and the second relay substrate 310C2 can be reduced. For example, the size (length) of each of the first relay substrate 310C1 and the second relay substrate 310C2 can be made smaller (shorter) than the relay substrate 310C shown in FIG. 22.

In this way, in the present modification example, the relay substrate 310C can be configured by combining relay substrates having a small size with each other. For that reason, according to the present modification example, the manufacturing suitability can be improved, and the increase in cost resulting from the increase in size can be suppressed.

Additionally, according to the radiographic imaging apparatus 1 of the present modification example, since the connecting portion 329 does not overlap the sensor substrate 12, the portion of the radiographic imaging apparatus 1 corresponding to the sensor substrate 12 can be made thinner.

Additionally, according to the radiographic imaging apparatus 1 of the present modification example, whether the driving IC 204 is disposed at any position of the front and back of the flexible cable 206 is easily set to the same position as in a case where the relay substrate 310C is not folded.

In addition, the length of each of the first relay substrate 310C1 and the second relay substrate 310C2 is not limited to the present modification example, but as described above, it is preferable that the connecting portion 329 has such a length that the connecting portion 329 does not overlap the sensor substrate 12.

Figure 25:
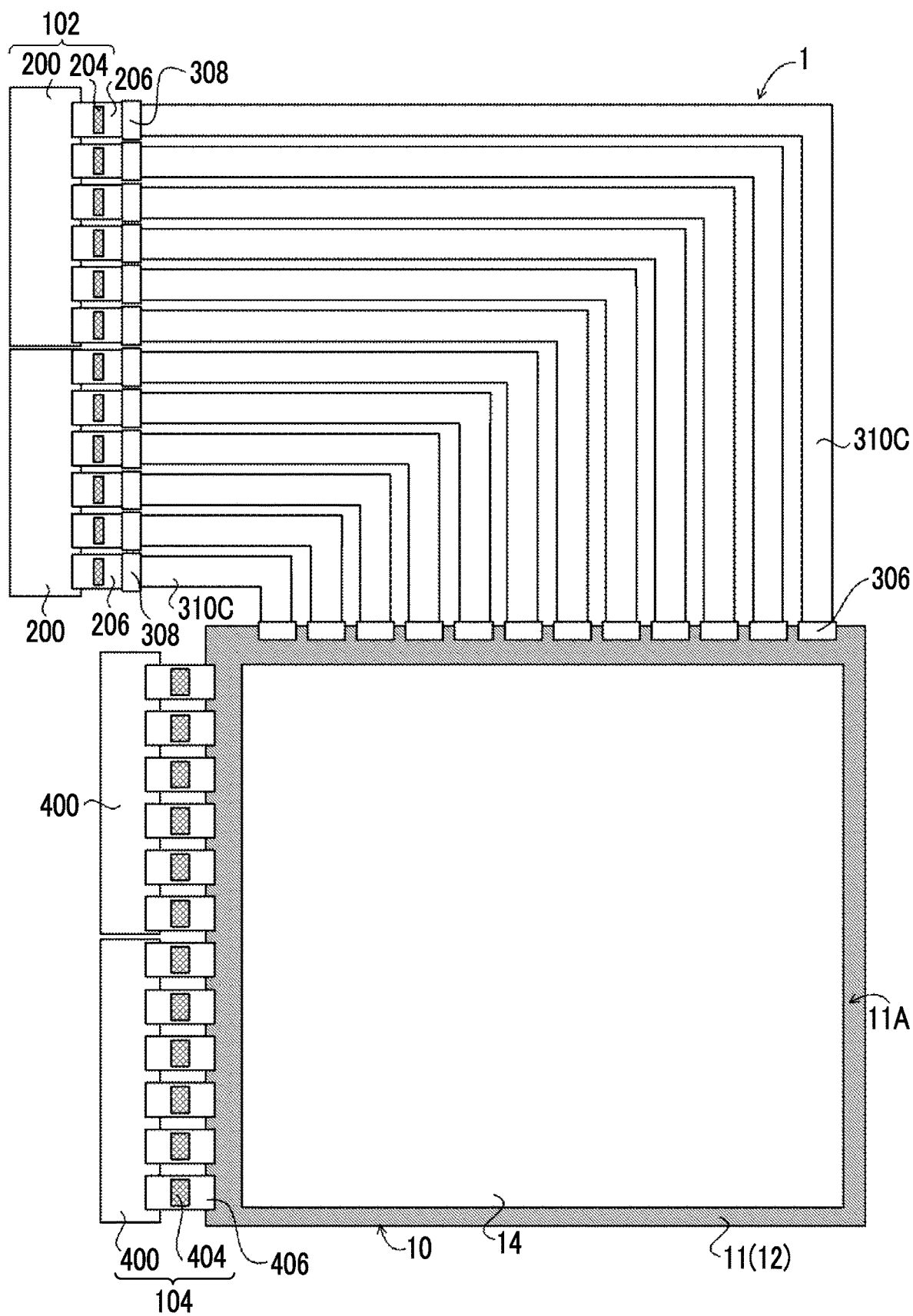
FIG. 25 is a plan view of another example of the radiographic imaging apparatus of Modification Example 2 as seen from the second surface side of the base material.

In addition, as shown in FIG. 25, a form may be adopted in which the relay substrate 310C is connected to the scanning wiring line 38 of the sensor substrate 12 via the connector 306 instead of being connected to the sensor substrate 12 by the thermocompression bonding. Additionally, a form may be adopted in which the relay substrate 310C is connected to the driving substrate 200 via the connector 308 instead of being connected to the driving substrate 200 by the thermocompression bonding. Examples of such connectors 306 and 308 include a zero insertion force (ZIF) structure connector and a Non-ZIF structure connector.

In this way, by performing at least one of the connection between the relay substrate 310C and the sensor substrate 12 or the connection between the relay substrate 310C and the flexible cable 206 by each of the connectors 306 or 308, in the radiographic imaging apparatus 1 of the present modification example, the handling becomes easy even in a case where the relay substrate 310C becomes long.

In addition, a form may be adopted in which the connection between the second relay substrate 310C2 and the first relay substrate 310C1 and the connection between the second relay substrate 310C2 and the flexible cable 206 in the radiographic imaging apparatus 1 shown in FIGS. 23 and 24 are also performed via a connector instead of being performed by the thermocompression bonding.

Figure 13:
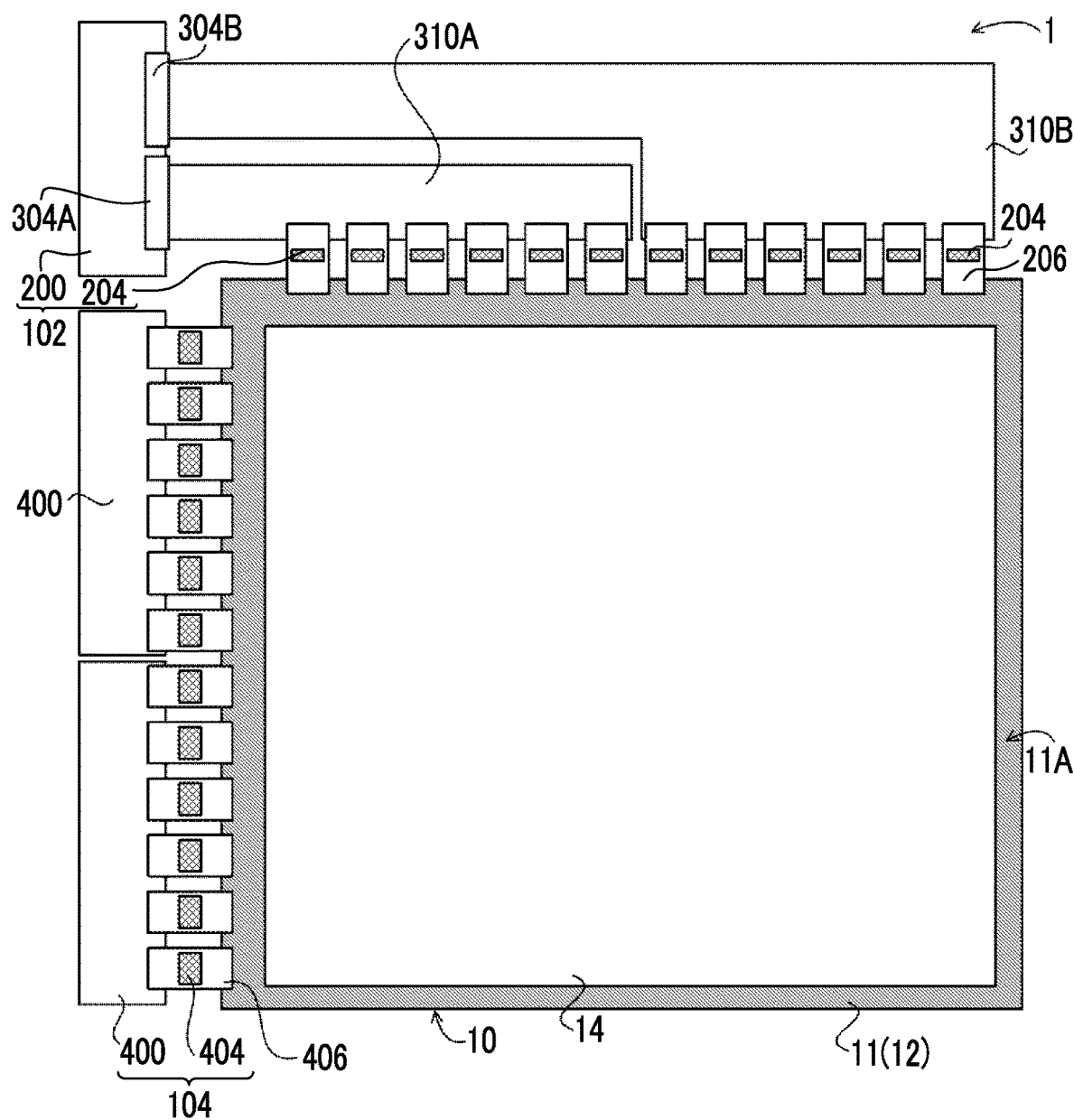
FIG. 13 is a plan view of another example of the radiographic imaging apparatus of the second embodiment as seen from the second surface side of the base material.

Additionally, for example, also in the relay substrates 310 (310A and 310B) of the radiographic imaging apparatus 1 of the present embodiment shown in FIGS. 12 and 13, a form may be adopted in which the relay substrate 310 is connected to the flexible cable 206 via a connector instead of being connected by the thermocompression bonding. Additionally, on the contrary, a form may be adopted in which the relay substrate 310 is connected to the driving substrate 200 by the thermocompression bonding instead of being connected to the driving substrate 200 by the connectors 304 (304A and 304B).

Third Embodiment

Figure 26:
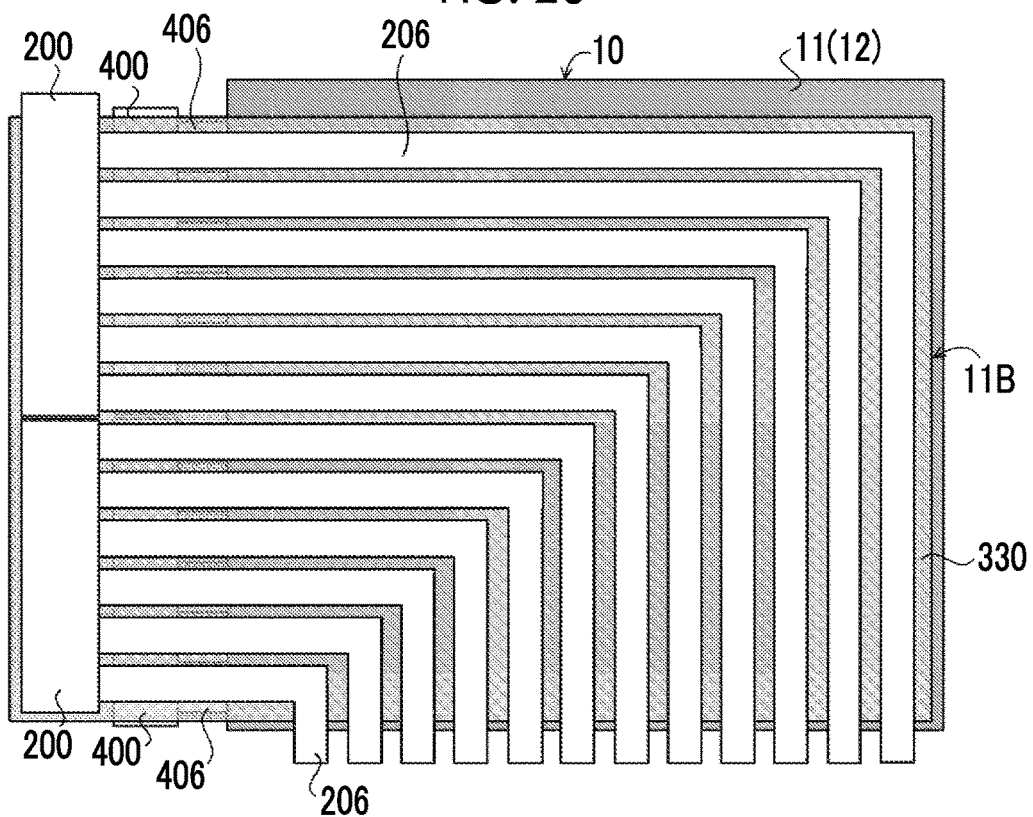
FIG. 26 is a plan view of an example of a radiographic imaging apparatus according to a third embodiment as seen from the second surface side of the base material.
Figure 27:
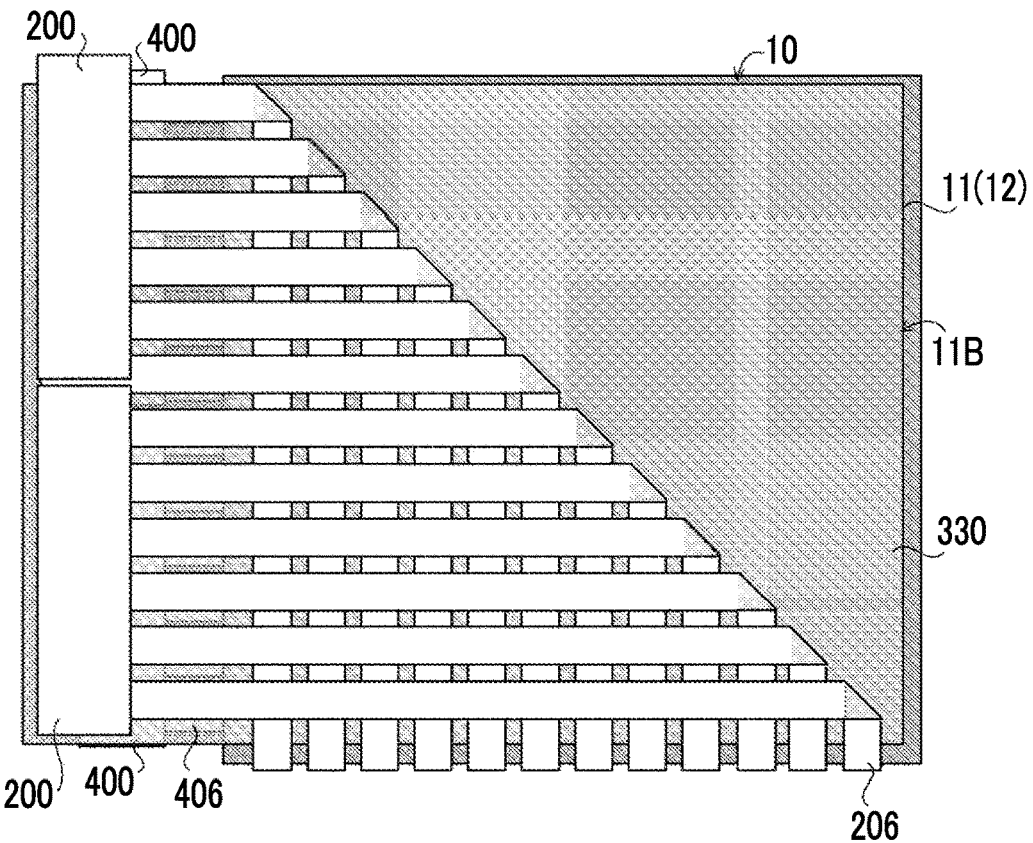
FIG. 27 is a plan view of another example of the radiographic imaging apparatus of the second embodiment as seen from the second surface side of the base material.

Next, a third embodiment will be described. FIGS. 26 and 27 show plan views of the radiographic imaging apparatus 1 of the present embodiment as seen from the second surface 11B side of the base material 11. FIG. 26 shows an example of a form including the L-shaped flexible cable 206, similarly to the flexible cable 206 of the first embodiment (refer to FIG. 4). Additionally, FIG. 27 shows an example of a form in which the flexible cable 206 having a straight shape is provided, similarly to the flexible cable 206 (refer to FIG. 7) of the radiographic imaging apparatus 1 of Modification example 1-1.

As shown in FIGS. 26 and 27, the radiographic imaging apparatus 1 of the present embodiment comprises a shielding member 330 between the first surface 11A of the base material 11 (sensor substrate 12) and the flexible cable 206. Additionally, the shielding member 330 of the present embodiment is also provided between the driving substrate 200 and the signal processing substrate 400 and between the driving IC 204 and the signal processing IC 404.

The shielding member 330 is a member that shields at least one of electricity, magnetism, or radiation. Examples of the material of the shielding member 330 include copper and Alpet (registered trademark).

The current flowing through the flexible cable 406 via the signal wiring line 36 due to an electric charge read from a pixel 30 is generally an extremely small current on the order of several fA to several pA or the like. In a case where this current is converted into a voltage by a charge amplifier included in the signal processing substrate 400 and then A/D converted, this signal is an extremely small minute electrical signal (hereinafter referred to as "read signal") of several tens of µV per bit). On the other hand, the potential of a drive signal flowing through the scanning wiring line 38 via the flexible cable 206 is 20 V to 40 V, which is an extremely large voltage as compared to the read signal. For that reason, in a case where the signal processing substrate 400 and the driving substrate 200 overlap each other or are disposed extremely close to each other, there is a concern that noise may be overlapped with the read signal due to the influence of electromagnetic induction by the drive signal on the flexible cable 406.

Thus, in the radiographic imaging apparatus 1 of the present embodiment, the shielding member 330 that shields at least one of electricity or magnetism is provided between the driving IC 204 and the signal processing IC 404 and between the driving substrate 200 and the signal processing substrate 400. Accordingly, the influence of the electromagnetic induction can be suppressed, and the overlap of noise with the read signal can be suppressed.

Additionally, there is a case where the flexible cable 206 generates backscattered rays and the flexible cable 206 is reflected in the radiographic image generated by the radiation detector 10. Thus, in the radiographic imaging apparatus 1 of the present embodiment, the shielding member 330 that shields the radiation that is the backscattered rays is provided between the flexible cable 206 and the sensor substrate 12. Accordingly, the reflection of the flexible cable 206 in the radiographic image can be suppressed.

As described above, in the radiographic imaging apparatus 1 of each of the above embodiments, the sensor substrate 12 on which the plurality of pixels 30 that accumulate the electric charges generated in response to the light converted from the radiation are formed, and the conversion layer 14 that is provided on the first surface 11A of the base material 11 to convert the radiation into light are provided in the pixel region 35 of the first surface 11A of the flexible base material 11. Additionally, the radiographic imaging apparatus 1 comprises the signal processing substrate 400 that is provided on one side of a pair of sides of the sensor substrate facing each other 12 and comprises at least a part of the circuit of the signal processing unit 104 to which electrical signals according to the electric charges accumulated in the plurality of pixels 30 of the sensor substrate 12 are input and which generates and outputs the image data according to the input electrical signals, and the driving substrate 200 that is provided on the one side or the other side of the pair of sides of the sensor substrate 12 and comprises at least a part of the circuit of the drive unit 102 that outputs a drive signal for outputting the accumulated electric charge from each of the plurality of pixels 30 of the sensor substrate 12 to each of the plurality of pixels 30. Moreover, the radiographic imaging apparatus 1 comprises the flexible cable 406 of which one end is provided along the one side of the pair of sides of the sensor substrate 12 and is electrically connected to the sensor substrate 12 and the other end is electrically connected to the signal processing substrate 400, and the flexible cable 206 of which one end is provided along a side intersecting the one side of the pair of sides of the sensor substrate 12, is electrically connected to the sensor substrate 12, and passes through the first surface 11A side of the base material 11 or the second surface 11B side opposite to the first surface 11A of the base material 11 and the other end is electrically connected to the driving substrate 200.

In this way, according to the radiographic imaging apparatus 1 of each of the above present embodiments, the flexible cable 206 connected to the sensor substrate 12 passes through the first surface 11A side of the base material 11 or the second surface 11B side opposite to the first surface 11A of the base material 11 and is electrically connected to the driving substrate 200. Accordingly, the driving substrate 200 can be disposed on the side of the sensor substrate 12 on the same side as the signal processing substrate 400 or on the side of the sensor substrate 12 facing the side to which the signal processing substrate 400 is connected.

Therefore, according to the radiographic imaging apparatus 1 of each of the above embodiments, a portion of the radiographic imaging apparatus 1 corresponding to the sensor substrate 12 can be made thinner.

Additionally, for example, in the case of a form in which a wiring line such as the scanning wiring line 38 is extended and connected to the driving substrate 200 in the sensor substrate 12 instead of the flexible cable 206 of each of the above embodiments, the wiring line provided in the sensor substrate 12 has a relatively small film thickness of about several hundred nm, high resistance is generated even in a case where the wiring length is short. In contrast, in a case where the externally attached flexible cable 206 of the sensor substrate 12 is used as in each of the above embodiments, the film thickness is about several um to several tens of µm, which is 10 to 100 times or more the thickness of the above wiring line. Therefore, low resistance can be generated. Additionally, since the flexible cable 206 can be wired using copper having a resistivity lower than that of the wiring material in the sensor substrate 12, the so-called wiring resistance can also be lowered.

Additionally, according to the radiographic imaging apparatus 1 of each of the above embodiments, the end portion of the flexible cable 206 may be connected to the outer edge of the sensor substrate 12, and the flexible cable 206 is folded. Therefore, the increase in size of the radiographic imaging apparatus 1 can be suppressed. In particular, the increase in area of the sensor substrate 12 of the radiographic imaging apparatus 1 can be suppressed.

And, for example, in a case where the scanning wiring line 38 is extended and the sensor substrate 12 itself is bent at the extended portion of the scanning wiring line 38, the wiring line provided in the sensor substrate 12 has a relatively small film thickness of about several hundred nm. Therefore, there is a concern that the scanning wiring line 38 may be broken due to metal fatigue caused by vibration or the like. In contrast, according to the radiographic imaging apparatus 1 of each of the above embodiments, in a case where the flexible cable 206 or the relay substrate 310 is bent, the film thickness of the wiring line is about several μm to several tens of μm, a reinforcing base material can also be disposed, and the sensor substrate 12 itself is not bent. Therefore, concerns about disconnection is suppressed.

Figure 28:
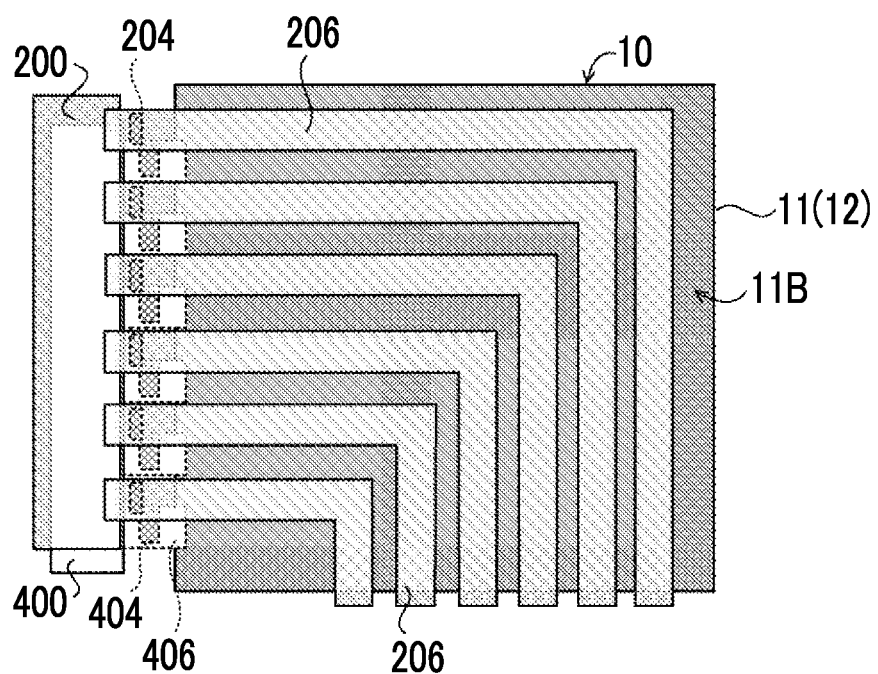
FIG. 28 is a plan view of another example of the radiographic imaging apparatus according to the embodiment as seen from the second surface side of the base material.

In addition, as shown in FIG. 28, it is preferable that the circuit components and the driving IC 204 mounted on the driving substrate 200 and the circuit components and the signal processing IC 404 mounted on the signal processing substrate 400 in the radiographic imaging apparatus 1 of each of the above embodiments are disposed in a non-overlapping state. As described above, the drive signal has an extremely large voltage as compared to the read signal, and the closer each of the driving substrate 200 and the driving IC 204 is to each of the signal processing substrate 400 and the signal processing IC 404, there is a higher concern that noise is overlapped with the read signal due to the influence of the electromagnetic induction by the drive signal. Meanwhile, as in the radiographic imaging apparatus 1 shown in FIG. 28, the circuit components and the driving IC 204 mounted on the driving substrate 200 and the circuit components and the signal processing IC 404 mounted on the signal processing substrate 400 do not overlap each other. Accordingly, the overlap of the above noise with the read signal can be suppressed.

In addition, the state in which the circuit components and the driving IC 204 mounted on the driving substrate 200 and the circuit components and the signal processing IC 404 mounted on the signal processing substrate 400 do not overlap each other is not limited to the form shown in FIG. 28. For example, a form may be adopted in which any one of the driving substrate 200 and the driving IC 204 and the signal processing substrate 400 and the signal processing IC 404 is disposed at a position close to the sensor substrate 12 and the other may be disposed at a position away from the sensor substrate 12.

That is, as long as at least a part of the driving IC 204 and at least a part of the signal processing IC 404 do not overlap each other, the overlap of noise with the read signal can be suppressed regardless of a specific form. In addition, from the viewpoint of suppressing the overlap of noise with the read signal, it is more preferable that the entire circuit such as the driving IC 204 included in the drive unit 102 and the entire circuit such as the signal processing IC 404 included in the signal processing unit 104 do not overlap each other.

Figure 29:
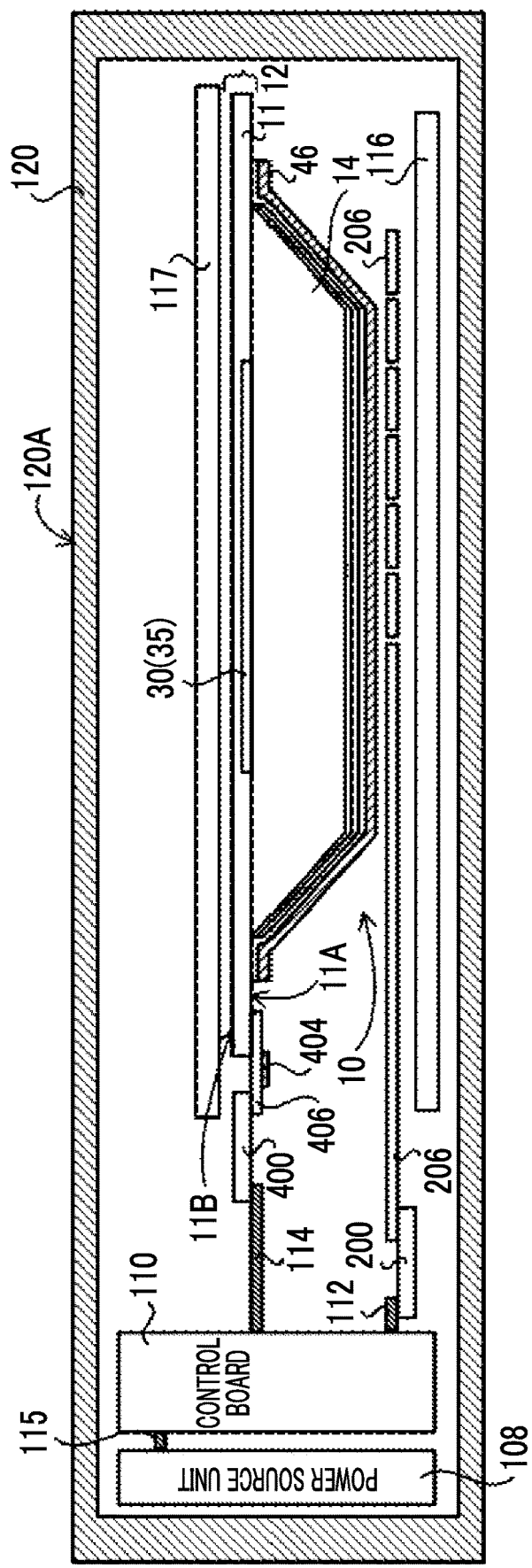
FIG. 29 is a cross-sectional view of an example of the radiographic imaging apparatus according to the embodiment housed in a housing.
Figure 30:
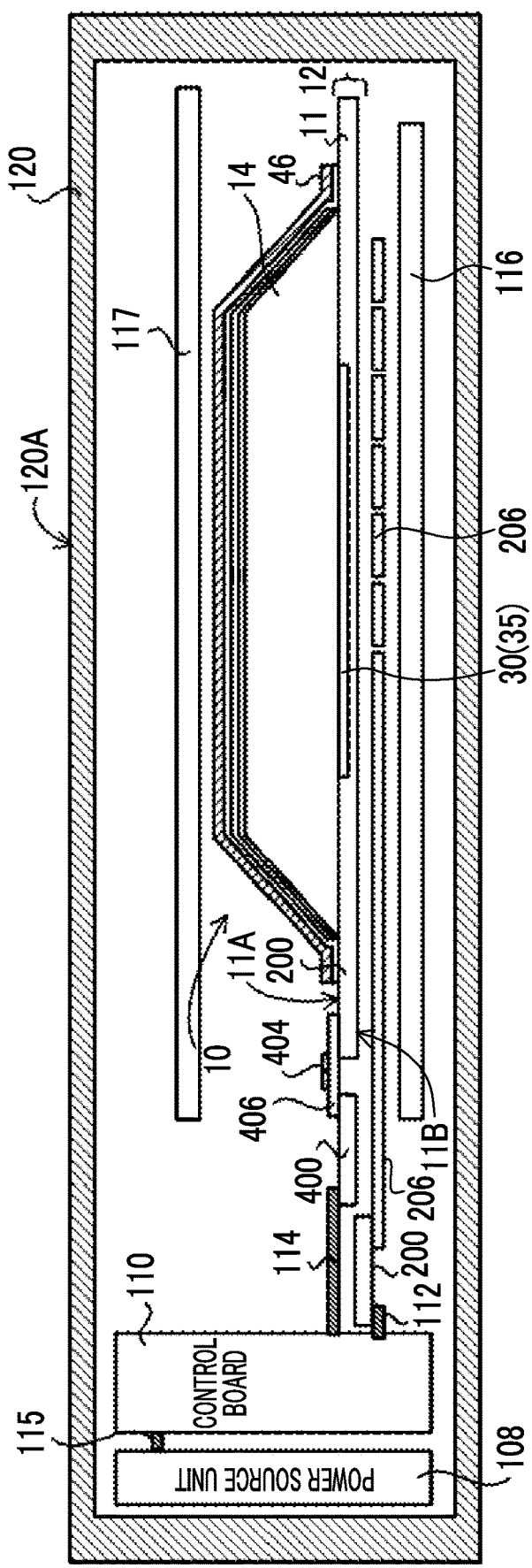
FIG. 30 is a cross-sectional view of another example of the radiographic imaging apparatus of the embodiment housed in the housing.

In addition, as shown in FIGS. 29 to 31, the radiation detector 10 and the like of the radiographic imaging apparatus 1 of each of the above embodiments is used while being housed in the housing 120.

FIG. 29 shows a cross-sectional view of an example of the ISS type radiographic imaging apparatus 1. As shown in FIG. 29, the radiation detector 10, the power source unit 108, and a control substrate 110 are provided side by side in a direction intersecting an incidence direction of radiation within the housing 120. The radiation detector 10 is disposed in a state in which the first surface 11A of the base material 11 in the sensor substrate 12 faces a top plate on an irradiation surface 120A side of the housing 120 that is irradiated with the radiation transmitted through a subject.

Additionally, FIG. 30 shows a cross-sectional view pf an example of the PSS type radiographic imaging apparatus 1 is shown. As shown in FIG. 30, the radiation detector 10, the power source unit 108, and a control substrate 110 are provided side by side in a direction intersecting an incidence direction of radiation within the housing 120. The radiation detector 10 is disposed in a state in which the second surface 11B of the base material 11 in the sensor substrate 12 faces an irradiation surface 120A side of the housing 120 that is irradiated with the radiation transmitted through a subject.

The control substrate 110 and the driving substrate 200 are connected to each other by a flexible cable 112. Additionally, the control substrate 110 and the signal processing substrate 400 are connected to each other by a flexible cable 114.

Additionally, the control substrate 110 is connected to the power source unit 108, which supplies electrical power to the image memory 106, the control unit 100, and the like that are formed in the control substrate 110, by a power source line 115.

A sheet 116 is further provided on a side from which the radiation transmitted through the radiation detector 10 is emitted, within the housing 120 of the radiographic imaging apparatus 1 shown in FIGS. 29 and 30. The sheet 116 is, for example, a copper sheet. The copper sheet does not easily generate secondary radiation due to incident radiation, and therefore, has a function of preventing scattering to the rear side, that is, the conversion layer 14 side. In addition, it is preferable that the sheet 116 covers at least an entire surface of the conversion layer 14 from which radiation is emitted, and covers the entire conversion layer 14.

Additionally, a protective layer 117 is further provided on a side (irradiation surface 120A side) on which radiation is incident, within the housing 120 of the radiographic imaging apparatus 1 shown in FIGS. 29 and 30. As the protective layer 117, moistureproof films, such as an ALPET (registered trademark) sheet obtained, a Parylene (registered trademark) film, and an insulating sheet, such as polyethylene terephthalate, can be applied to an insulating sheet (film). The protective layer 117 has a moistureproof function and an antistatic function with respect to the pixel array 31. For that reason, it is preferable that the protective layer 117 covers at least the entire surface of the pixel array 31 on the side on which radiation is incident, and it is preferable to cover the entire surface of the sensor substrate 12 on the side on which radiation is incident.

As shown in the example shown in FIGS. 29 and 30, there are many cases where each of the power source unit 108 and the control substrate 110 is thicker than the radiation detector 10. In such a case, as in the example shown in FIG. 30, the thickness of the portion of the housing 120 in which the radiation detector 10 is provided may be smaller than the thickness of the portion of the housing 120 in which each of the power source unit 108 and the control substrate 110 is provided. In addition, in this way, in a case where the thickness of the portion of the housing 120 in which each of the power source unit 108 and the control substrate 110 is provided and the thickness of the portion of the housing 120 in which the radiation detector 10 is provided are made different, and in a case where a step is generated at a boundary part between the two portions, there is a concern that a sense of discomfort may be given to a subject who comes into contact with a boundary part 120B. Therefore, the form of the boundary part 120B is preferably in a state of having an inclination.

Accordingly, it is possible to construct an ultra-thin portable electronic cassette according to the thickness of the radiation detector 10.

Additionally, for example, in this case, the materials of the housing 120 may be different in the portion of the housing 120 in which each of the power source unit 108 and the control substrate 110 is provided and the portion of the housing 120 in which the radiation detector 10 is provided. Moreover, for example, the portion of the housing 120 in which each of the power source unit 108 and the control substrate 110 is provided and the portion of the housing 120 in which the radiation detector 10 is provided may be separated configured.

Additionally, as described above, the housing 120 is preferably made of a material having a low absorbance of radiation R, particularly X-rays and a high stiffness, and is preferably made of a material having a sufficiently high modulus of elasticity. However, a portion corresponding to the irradiation surface 120A of the housing 120 may be made of a material having a low absorbance of the radiation R, a high stiffness, and a sufficiently high modulus of elasticity, and the other portions may be made of a material different from the portion corresponding to the irradiation surface 120A, for example, a material having a lower modulus of elasticity than the portion of the irradiation surface 120A.

In addition, in each of the above embodiments, a form in which the driving substrate 200 and the signal processing substrate 400 are provided on the same side of the sensor substrate 12 has been described. However, the disposition of the driving substrate 200 and the signal processing substrate 400 is not limited to the described form. For example, the driving substrate 200 may be provided on the side of the sensor substrate 12 opposite to the side on which the signal processing substrate 400 is provided. In addition, in this case, since the power source unit 108 and the like are provided on both the driving substrate 200 side and the signal processing substrate 400 side, both sides of the sensor substrate 12 facing each other are thicker than the portion of the sensor substrate 12. However, even in such a form, since the flexible cable 206 only passes through the portion of the sensor substrate 12, the thickness of the radiographic imaging apparatus 1 can be reduced in the portion of the sensor substrate 12.

Additionally, the radiographic imaging apparatus 1 is not limited to each of the above embodiments, and may have, for example, a form in which the flexible cable 206 and the driving substrate 200 are connected to each other via another flexible cable. In this case, since the flexible cable 206 remains short in the manufacturing process of the radiographic imaging apparatus 1, the radiation detector 10 can be easily handled.

Additionally, in the above respective embodiments, as shown in FIG. 1, an aspect in which the pixels 30 are two-dimensionally arranged in a matrix has been described. However, the invention is not limited to the aspect, and for example, the pixels 30 may be one-dimensionally arranged or may be arranged in a honeycomb shape. Additionally, the shape of the pixels 30 is also not limited, and may be a rectangular shape, or may be a polygonal shape, such as a hexagonal shape. Moreover, it goes without saying that the shape of the pixel array 31 (pixel region 35) is also not limited.

Additionally, the position where the driving IC 204 and the flexible cable 406 are mounted is not limited to each of the above embodiments. That is, whether the driving IC 204 is mounted on any of the front and back of the flexible cable 206 and the specific mounting position are not limited to each of the above embodiments. Additionally, whether the signal processing IC 404 is executed on any of the front and back of the flexible cable 406 and the specific mounting position are not limited to each of the above embodiments.

Additionally, the shape or the like of the conversion layer 14 is not limited to the above respective embodiments. In the above respective embodiments, an aspect in which the shape of the conversion layer 14 is a rectangular shape similarly to the shape of the pixel array 31 (pixel region 35) has been described. However, the shape of the conversion layer 14 may not be the same shape as the pixel array 31 (pixel region 35). Additionally, the shape of the pixel array 31 (pixel region 35) may not be a rectangular shape but may be, for example, other polygonal shapes or a circular shape.

In addition, it goes without saying that the configurations and the like of the radiographic imaging apparatuses 1 and the radiation detectors 10 that are described in the above respective embodiments are merely examples, and can be changed in response to situations without departing from the scope of the present invention.

The disclosure of Japanese Patent Application No. 2019-069077 filed on Mar. 29, 2019 and the disclosure of Japanese Patent Application No. 2019-239567 filed on Dec. 27, 2019 are incorporated into the present specification in their entirety by reference.

All documents, patent applications, and technical standards described in the present specification are incorporated in the present specification by reference in their entireties to the same extent as in a case where the individual documents, patent applications, and technical standards are specifically and individually written to be incorporated by reference.

What is claimed is:

1. A radiographic imaging apparatus comprising:
    a sensor substrate in which a plurality of pixels for accumulating electric charges generated in response to light converted from radiation is formed in a pixel region of a first surface of a flexible base material;
    a conversion layer that is provided on the first surface of the base material to convert the radiation into light;
    a signal processing substrate that is provided on one side of a pair of sides of the sensor substrate facing each other and includes at least a part of a circuit of a signal processing unit to which electrical signals according to the electric charges accumulated in the plurality of pixels of the sensor substrate are input and which generates and outputs image data according to the input electrical signals;
    a driving substrate that is provided on the one side or the other side of the pair of sides of the sensor substrate and includes at least a part of a circuit of a drive unit that outputs a drive signal for outputting the accumulated electric charge from each of the plurality of pixels of the sensor substrate, to each of the plurality of pixels;
    a first cable of which one end is provided along the one side of the pair of sides of the sensor substrate and is electrically connected to the sensor substrate and the other end is electrically connected to the signal processing substrate; and
    a second cable of which one end is provided along a side intersecting the one side of the pair of sides of the sensor substrate, is electrically connected to the sensor substrate, and passes through the first surface side of the base material or a second surface side opposite to the first surface of the base material and the other end is electrically connected to the driving substrate.

2. The radiographic imaging apparatus according to claim 1,
    wherein the second cable has a straight shape extending in a straight line, is bent in a direction in which the second cable is folded with respect to an extending direction of the second cable, and is further bent in a direction intersecting the extending direction of the second cable.

3. The radiographic imaging apparatus according to claim 1,
    wherein the second cable includes a portion that includes one end of the second cable connected to the sensor substrate and extends in a first direction intersecting a direction of the side of the sensor substrate to which the second cable is connected, and a portion that includes the other end of the second cable connected to the driving substrate and extends in a second direction that intersects the first direction.

4. The radiographic imaging apparatus according to claim 1,
wherein the first cable is mounted with a part of a signal processing circuit, which is not included in the signal processing substrate, in the circuit of the signal processing unit, and
the second cable is mounted with a part of a drive circuit, which is not included in the driving substrate, in the circuit of the drive unit.

5. The radiographic imaging apparatus according to claim 4,
wherein the part of the signal processing circuit and the part of the drive circuit are disposed at positions where the parts do not overlap each other.

6. The radiographic imaging apparatus according to claim 1;
wherein the circuit of the signal processing unit and the circuit of the drive unit are disposed at positions where the circuits do not overlap each other.

7. The radiographic imaging apparatus according to claim 1,
wherein one end of the second cable is electrically connected to the sensor substrate by a connector at the intersecting side of the sensor substrate.

8. The radiographic imaging apparatus according to claim 1,
wherein the other end of the second cable is electrically connected to the driving substrate by a connector.

9. The radiographic imaging apparatus according to claim 1,
wherein the number of the second cables electrically connected to the driving substrate is smaller than the number of the second cables electrically connected to the sensor substrate.

10. The radiographic imaging apparatus according to claim 1, further comprising:
a relay substrate that is electrically connected to the driving substrate,
wherein the other end of the second cable is electrically connected to the relay substrate instead of the driving substrate.

11. The radiographic imaging apparatus according to claim 10, further comprising:
a plurality of the second cables having a larger number than the number of the relay substrates.

12. The radiographic imaging apparatus according to claim 10,
wherein the relay substrate is electrically connected to at least one of the other end of the second cable or the driving substrate by a connector.

13. The radiographic imaging apparatus according to claim 10,
wherein the relay substrate includes a first relay portion that is electrically connected to the second cable, and an L-shaped second relay portion having a long side that extends along a side of the sensor substrate to which the second cable is electrically connected, and a short side that extends in a direction intersecting the direction in which the long side extends and is electrically connected to the driving substrate.

14. The radiographic imaging apparatus according to claim 13,
wherein the short side of the second relay portion is bent in the direction in which the long side extends.

15. The radiographic imaging apparatus according to claim 10,
wherein the relay substrate includes a first relay portion that is electrically connected to the second cable, a second relay portion that extends along a side of the sensor substrate to which the second cable is electrically connected, and a third relay portion of which one end is electrically connected to an end portion of the second relay portion and the other end is electrically connected to the driving substrate.

16. The radiographic imaging apparatus according to claim 15,
wherein a connecting portion by which the end portion of the second relay portion and the one end of the third relay portion are electrically connected is provided in a region that does not overlap the sensor substrate.

17. The radiographic imaging apparatus according to claim 10,
wherein the relay substrate has flexibility.

18. The radiographic imaging apparatus according to claim 1, further comprising:
a relay substrate that is electrically connected to the sensor substrate,
wherein one end of the second cable is electrically connected to the relay substrate instead of the sensor substrate.

19. The radiographic imaging apparatus according to claim 18
wherein the relay substrate is electrically connected to at least one of one end of the second cable or the sensor substrate by a connector.

20. The radiographic imaging apparatus according to claim 18,
wherein the relay substrate includes a first relay substrate of which one end is electrically connected to the sensor substrate and a second relay substrate of which one end is electrically connected to the other end of the first relay substrate.

21. The radiographic imaging apparatus according to claim 20,
wherein a connecting portion by which the first relay substrate and the second relay substrate are electrically connected to each other is provided in a region that does not overlap the sensor substrate.

22. The radiographic imaging apparatus according to claim 1,
wherein a shielding member that shields at least one of electricity, magnetism, or radiation is provided between the second cable and the first surface side of the base material through which the second cable passes or the second surface side.

23. The radiographic imaging apparatus according to claim 22,
wherein the shielding member is also provided between the circuit of the signal processing unit and the circuit of the drive unit.

24. The radiographic imaging apparatus according to claim 1, further comprising:
a housing that houses the sensor substrate, the conversion layer, the signal processing substrate, the driving substrate, the first cable, and the second cable.

25. The radiographic imaging apparatus according to claim 24,
wherein the housing has an irradiation surface to be irradiated with the radiation, and the second cable passes between a surface of the housing opposite to the irradiation surface and a laminate in which the conversion layer is formed on the sensor substrate.

* * * * *